United States Patent
Faaborg et al.

(10) Patent No.: US 9,766,959 B2
(45) Date of Patent: Sep. 19, 2017

(54) DETERMINING USER RESPONSE TO NOTIFICATIONS BASED ON A PHYSIOLOGICAL PARAMETER

(71) Applicant: Google Inc., Mountain View, CA (US)

(72) Inventors: Alexander Faaborg, Mountain View, CA (US); Gabriel Aaron Cohen, Alameda, CA (US); Austin Robison, Sunnyvale, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/244,514

(22) Filed: Apr. 3, 2014

(65) Prior Publication Data

US 2015/0269009 A1   Sep. 24, 2015

Related U.S. Application Data

(60) Provisional application No. 61/954,909, filed on Mar. 18, 2014.

(51) Int. Cl.
*G06F 3/00* (2006.01)
*G06F 9/44* (2006.01)
(Continued)

(52) U.S. Cl.
CPC .............. *G06F 9/546* (2013.01); *A61B 5/024* (2013.01); *A61B 5/0205* (2013.01);
(Continued)

(58) Field of Classification Search
CPC ...................................................... G06F 9/546
(Continued)

(56) References Cited

U.S. PATENT DOCUMENTS 8,131,848 B1 * 3/2012 Denise .......................... 709/224
8,347,326 B2   1/2013 Weitzenfeld et al.
(Continued)

FOREIGN PATENT DOCUMENTS

EP    1 379 064 A2    1/2004
JP    2005031267 A    2/2005
(Continued)

OTHER PUBLICATIONS

"Bandu: The watch that gives you time to relax," indiegogo [online]. First accessed on Jun. 13, 2013. Retrieved from internet: <www.indiegogo.com/projects/bandu-the-watch-that-gives-you-time-to-relax>, 15 pages.
(Continued)

*Primary Examiner* — Timothy A Mudrick
(74) *Attorney, Agent, or Firm* — Shumaker & Sieffert, P.A.

(57) ABSTRACT

In some examples, a technique may include outputting information associated with a notification. The notification may be associated with a notification attribute. The technique may further include determining, by a computing device, that a user has perceived the information associated with the notification; and receiving, by the computing device, an indication of at least one physiological parameter representative of a reaction of the user to the information associated with the notification. In some examples, the technique also includes, responsive to receiving the indication of the at least one physiological parameter representative of the reaction of the user to the information associated with the notification, controlling, by the computing device, at least one notification configuration setting related to outputting information associated with other notifications associated with the notification attribute.

22 Claims, 8 Drawing Sheets

(51) Int. Cl.

| | |
|---|---|
| *G06F 9/46* | (2006.01) |
| *G06F 13/00* | (2006.01) |
| *G06F 9/54* | (2006.01) |
| *G06F 3/16* | (2006.01) |
| *H04L 12/58* | (2006.01) |
| *A61B 5/0484* | (2006.01) |
| *G06F 3/048* | (2013.01) |
| *A61B 5/00* | (2006.01) |
| *A61B 5/0205* | (2006.01) |
| *A61B 5/053* | (2006.01) |
| *A61B 5/16* | (2006.01) |
| *A61B 5/024* | (2006.01) |

(52) U.S. Cl.
CPC .......... *A61B 5/0484* (2013.01); *A61B 5/0533* (2013.01); *A61B 5/165* (2013.01); *A61B 5/486* (2013.01); *A61B 5/6898* (2013.01); *G06F 3/048* (2013.01); *G06F 3/162* (2013.01); *H04L 51/24* (2013.01); *A61M 2230/005* (2013.01); *A61M 2230/04* (2013.01); *G06F 2203/011* (2013.01); *G06F 2209/547* (2013.01)

(58) Field of Classification Search
USPC ........................................................ 719/315
See application file for complete search history.

(56) References Cited

U.S. PATENT DOCUMENTS

| | | |
|---|---|---|
| 2002/0187794 A1 | 12/2002 | Fostick et al. |
| 2004/0203673 A1 | 10/2004 | Seligmann |
| 2005/0075934 A1 | 4/2005 | Knight et al. |
| 2005/0159190 A1 | 7/2005 | Dowling |
| 2005/0186977 A1 | 8/2005 | Chiu et al. |
| 2006/0071798 A1 | 4/2006 | Kiff et al. |
| 2006/0142968 A1 | 6/2006 | Han et al. |
| 2007/0087790 A1 | 4/2007 | Worick et al. |
| 2008/0235284 A1 | 9/2008 | Aarts et al. |
| 2009/0002178 A1 | 1/2009 | Guday et al. |
| 2009/0063255 A1 | 3/2009 | Pradeep et al. |
| 2009/0270170 A1 | 10/2009 | Patton |
| 2010/0086204 A1 | 4/2010 | Lessing |
| 2010/0240416 A1 | 9/2010 | Knight |
| 2010/0313048 A1 | 12/2010 | Shye et al. |
| 2011/0003665 A1 | 1/2011 | Burton et al. |
| 2011/0072509 A1 | 3/2011 | Mohanty |
| 2011/0084807 A1* | 4/2011 | Logan et al. ................ 340/10.1 |
| 2011/0126143 A1 | 5/2011 | Williams et al. |
| 2011/0131274 A1 | 6/2011 | Hille |
| 2011/0209181 A1 | 8/2011 | Gupta et al. |
| 2012/0052905 A1 | 3/2012 | Lim et al. |
| 2012/0083668 A1 | 4/2012 | Pradeep et al. |
| 2013/0082916 A1 | 4/2013 | Dixit |
| 2013/0154838 A1 | 6/2013 | Alameh et al. |
| 2013/0198694 A1* | 8/2013 | Rahman et al. .............. 715/864 |
| 2013/0331132 A1 | 12/2013 | Goliszewski et al. |
| 2014/0002375 A1 | 1/2014 | Rydenhag et al. |
| 2014/0007010 A1 | 1/2014 | Blom |
| 2014/0141816 A1* | 5/2014 | Winkler ........................ 455/457 |
| 2014/0280578 A1 | 9/2014 | Barat et al. |
| 2015/0035644 A1 | 2/2015 | June et al. |
| 2015/0074197 A1 | 3/2015 | Brown et al. |

FOREIGN PATENT DOCUMENTS

| | | |
|---|---|---|
| WO | 2004004295 A1 | 1/2004 |
| WO | 2010009774 A1 | 1/2010 |
| WO | 2012094021 A1 | 7/2012 |

OTHER PUBLICATIONS

Strauss, "$1.1 million-plus Gates grants: 'Galvanic' bracelets that measure student engagement," The Washington Post [online]. Jun. 11, 2012. Retrieved from the Internet: <www.washingtonpost.com/blogs/answer-sheet/post/11-million-plus-gates-grants-galvanic-bracelets-that-measure-student-engagement/2012/06/10/gJQAgAUbTV_blog.html>, 6 pages.

"Rationalizer," Phillips 2013 [online]. First accessed on Jun. 13, 2013. Retrieved from the Internet: <http://www.design.phillips.com/about/design/designportfolio/design_futures/reationlizer.page>, 1 page.

AffectivaQ, Hardware Manual, downloaded from www.affectiva.com/q-sensor, 66 pages, published on Mar. 29, 2013.

Affectiva, Liberate yourself from the lab: Q Sensor measures EDA in the wild, 11 pages, published 2012, downloaded from www.affectiva.com/q-sensor, downloaded on Apr. 3, 2014.

International Preliminary Report on Patentability and Written Opinion from International Application No. PCT/US2015/019714, mailed Sep. 29, 2016, 10 pp.

Response to Rules 161(1) and 162 EPC dated Nov. 23, 2016, from counterpart European Application No. 15711988.4, filed Jun. 6, 2017, 22 pages.

* cited by examiner

DETERMINING USER RESPONSE TO NOTIFICATIONS BASED ON A PHYSIOLOGICAL PARAMETER

This application claims the benefit of U.S. Provisional Application No. 61/954,909, filed Mar. 18, 2014, the entire content of which is hereby incorporated by reference.

BACKGROUND

Many modern computing devices (e.g., mobile telephones, wearable computing devices, etc.) are capable of receiving notification associated with a user of the computing device. For example, a computing device may receive notification data indicating that the computing device received a new instant message associated with an instant messaging account of the user. To alert the user to the receipt of the notification data and/or the new instant message indicated by the notification data, the computing device may output an alert (e.g., a visual, audible, and/or haptic type alert) based on the notification data to indicate to the user that the new instant message was received. Sometimes, the output of the alert may be perceived as a distraction, disruption, and/or annoyance, at a particular time.

SUMMARY

In some examples, the disclosure describes a method including outputting information associated with a notification, where the notification is associated with a notification attribute; determining, by a computing device, that a user has perceived the information associated with the notification; receiving, by the computing device, an indication of at least one physiological parameter representative of a reaction of the user to the information associated with the notification; and responsive to receiving the indication of the at least one physiological parameter representative of the reaction of the user to the information associated with the notification, controlling, by the computing device, at least one notification configuration setting related to outputting information associated with other notifications associated with the notification attribute.

In some examples, the disclosure describes A computing device including one or more processors and at least one module operable by the one or more processors. The at least one module may be operable by the one or more processors to output information associated with a notification, wherein the notification is associated with a notification attribute; determine that a user has perceived the information associated with the notification; receive an indication of at least one physiological parameter representative of a reaction of the user to the information associated with the notification; and responsive to receiving the indication of the at least one physiological parameter representative of the reaction of the user to the information associated with the notification, control at least one notification configuration setting related to outputting information associated with other notifications associated with the notification attribute.

In a further example, the disclosure describes a computer-readable storage medium comprising instructions that, when executed, configure one or more processors of a computing device to output information associated with a notification, wherein the notification is associated with a notification attribute; determine that a user has perceived the information associated with the notification; receive an indication of at least one physiological parameter representative of a reaction of the user to the information associated with the notification; and responsive to receiving the indication of the at least one physiological parameter representative of the reaction of the user to the information associated with the notification, control at least one notification configuration setting related to outputting information associated with other notifications associated with the notification attribute.

The details of one or more examples are set forth in the accompanying drawings and the description below. Other features, objects, and advantages will be apparent from the description and drawings, and from the claims.

DETAILED DESCRIPTION

Figure 1:
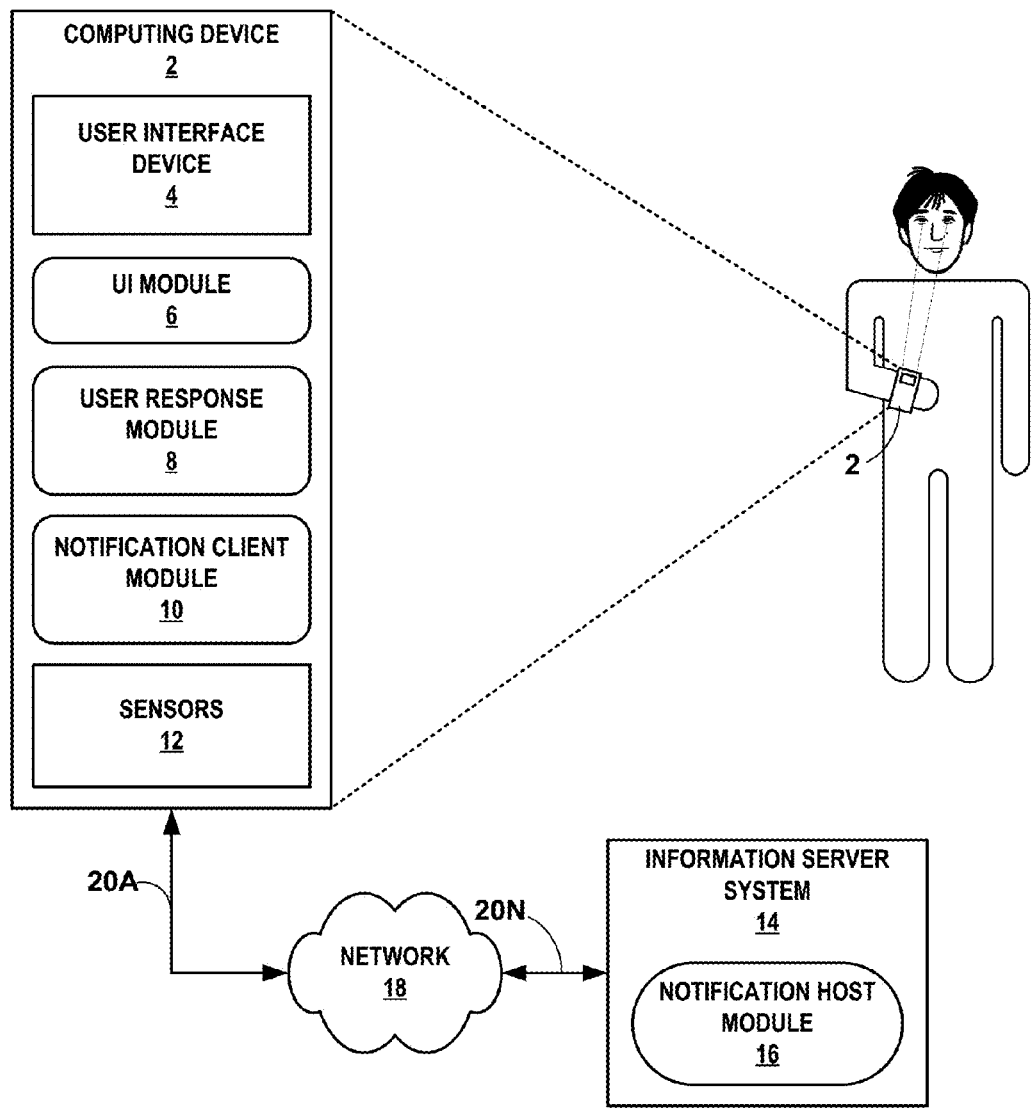
FIG. 1 is a block diagram illustrating an example computing device configured to determine a user reaction to information associated with a notification based on at least one physiological parameter, in accordance with one or more techniques of the present disclosure.

The disclosure describes techniques by which a computing device determines, based on at least one physiological parameter, a user's reaction to information associated with a notification and accordingly controls, based at least in part on the at least one physiological parameter, at least one notification configuration setting. The computing device may be configured to output information associated with a notification. For example, the computing device may receive information associated with a notification from an application or process executing at the computing device and/or from a server as part of a notification service (e.g., a notification service executing in a cloud computing environment, at a remote server device, etc.).

The computing device may be configured to output the information associated with the notification by, for example, outputting the information for display at a display device and/or as an audio signal for output by an audio output device. Responsive to outputting the information associated with the notification, the computing device may be configured to determine whether the user has perceived the information and to receive an indication of at least one physiological parameter that is indicative of the response of the user to the information. The at least one physiological parameter may include, for example, a heart rate of the user or a galvanic skin response (GSR) of the user. The indication of the at least one physiological parameter may originate from at least one physiological parameter sensor, which may be included in the computing device or operably coupled to the computing device.

The computing device may be configured to control, based on the indication of the at least one physiological parameter, at least one notification configuration setting related to outputting information associated with other notifications associated with a notification attribute. The notification attribute may be associated with the notification, and may include, for example, an application with which the notification is associated, an application type associated with the application with which the notification is associated, a sender from which the information associated with the notification originated, etc. For example, responsive to determining that at least one physiological parameter indicated that the user reacted negatively (e.g., was annoyed, angered, disappointed, etc.), the computing device may increase the prominence of a notification control panel setting related to notifications sharing the notification attribute. As another example, the computing device may output or modify a user interface element included in or adjacent to a visual representation of the information associated with the notification to allow a user to control output of future notifications associated with the notification attribute. For example, the computing device may output a toggle switch, a check box, or another user interface element that allows the user to indicate that notifications associated with the notification attribute should not be output in the future. As another example, responsive to determining that at least one physiological parameter indicated that the user reacted negatively, the computing device may be configured to disable future notifications associated with the notification attribute.

In this way, by controlling at least one notification configuration setting related to outputting information associated with other notifications associated with the notification attribute, the computing device may facilitate user control of notifications. For example, the techniques of this disclosure may facilitate user control of notifications settings in a way that may make it easier for the user to mute or disable notifications that cause a negative reaction, are overly interruptive, or are otherwise bothersome to the user. This may reduce inconvenience or negative reactions of the user in response to notifications and may facilitate customization of notification settings by the user.

Throughout the disclosure, examples are described where a computing device and/or a computing system may analyze information (e.g., locations, speeds, etc.) associated with a computing device only if the computing device receives permission from the user to analyze the information. For example, in situations discussed below in which the computing device may collect or may make use of information associated with the user, the user may be provided with an opportunity to provide input to control whether programs or features of the computing device can collect and make use of user information (e.g., information about a user's current location, current speed, etc.), or to dictate whether and/or how to the computing device may receive content that may be relevant to the user. In addition, certain data may be treated in one or more ways before it is stored or used by the computing device and/or computing system, so that personally identifiable information is removed. For example, a user's identity may be treated so that no personally identifiable information can be determined about the user, or a user's geographic location may be generalized where location information is obtained (such as to a city, ZIP code, or state level), so that a particular location of a user cannot be determined. Thus, the user may have control over how information is collected about the user and used by the computing device.

FIG. 1 is a block diagram illustrating an example computing device configured to determine a user reaction to information associated with a notification based on at least one physiological parameter, in accordance with one or more techniques of the present disclosure. As shown in the example of FIG. 1, computing device 2 includes user interface device 4, user interface ("UI") module 6, user response module 8, notification client module 10, and sensors 12. FIG. 1 also illustrated that computing device is communicatively coupled to an information server system 14 using network 18.

Network 18 may include any public or private communication network, for instance, a cellular, Wi-Fi®, and/or other type of network for transmitting data between computing devices. Computing device 2 and information server system 14 may send and receive data across network 18 using any suitable communication techniques. For example, computing device 2 may be operatively coupled to network 18 using network link 20A and information server system 14 may be operatively coupled to network 18 by network link 20N. Network 18 may include network hubs, network switches, network routers, etc., that are operatively intercoupled thereby providing for the exchange of information between computing device 2 and information server system 14. In some examples, network links 20A and 20N (collectively, "network links 20") may be Ethernet, ATM, or other network connections. Such connections may be wireless and/or wired connections.

Information server system 14 may include any suitable remote computing system, such as one or more desktop computers, laptop computers, mainframes, servers, cloud computing systems, etc. capable of sending and receiving information (e.g., information associated with notifications) across network link 20N to network 18. In some examples, information server system 14 may include a host server for a notification system service. One or more computing devices, such as computing device 2, may access a notification service hosted by information server system 14 for transmitting and/or receiving information associated with notifications between processes, platforms, applications, and services executing at the one or more computing devices. In some examples, information server system 14 may include a cloud computing system that provides notification services through network 18 to the one or more computing devices that access the notification services via access to the cloud provided by information server system 14.

In the example of FIG. 1, information server system 14 includes notification host module 16. Notification host module 16 may perform operations described herein using software, hardware, firmware, or a mixture of hardware, software, and/or firmware residing in and/or executing at information server system 14. In some examples, information server system 14 may execute notification host module 16 with multiple processors or multiple devices. Information server system 14 may execute notification host module 16 as a virtual machine executing on underlying hardware, as one or more services of an operating system or computing platform, as one or more executable programs at an application layer of a computing platform, etc.

Notification host module 16 may perform functions for routing notification data between one or more computing devices, such as computing device 2, over network 18.

Notification host module 16 may perform functions for hosting a notification service and outputting notification data for transmission to one or more computing devices, including computing device 2. For example, notification host module 16 may receive information associated with a notification that indicates a message was received by an instant messaging account associated with computing device 2 and may output the information associated with the notification for transmission across network 18 to computing device 2.

As described below, computing device 2 may output the information associated with the notification. In some examples, computing device 2 may receive notification data from notification host module 16 of information server system 14 via network links 20A.

In the example of FIG. 1, computing device 2 is a wearable computing (e.g., a computerized watch, computerized eyewear, computerized gloves, etc.). However, in other examples, computing device 2 may be a tablet computer, mobile phone, personal digital assistant (PDA), laptop computer, gaming system, media player, e-book reader, television platform, automobile navigation system, or any other type of mobile and/or non-mobile computing device that is configured to output information associated with a notification in accordance with techniques of this disclosure.

User interface device (UID) 4 of computing device 2 may function as respective input and/or output devices for computing device 2. UID 4 may be implemented using various technologies. For instance, UID 4 may function as an input device using a presence-sensitive input screen, such as a resistive touchscreen, a surface acoustic wave touchscreen, a capacitive touchscreen, a projective capacitance touchscreen, a pressure sensitive screen, an acoustic pulse recognition touchscreen, or another presence-sensitive display technology. UID 4 may function as an output (e.g., display) device using any one or more display devices, such as liquid crystal displays (LCD), dot matrix displays, light emitting diode (LED) displays, organic light-emitting diode (OLED) displays, e-ink, or similar monochrome or color displays capable of outputting visible information to a user of computing device 2. In some examples, the display devices may be physically separate from a presence-sensitive device included in computing device 2.

UID 4 may include a presence-sensitive display that may receive tactile input from a user of computing device 2. UID 4 may receive indications of tactile input by detecting one or more gestures from a user (e.g., the user touching or pointing to one or more locations of UID 4 with a finger or a stylus pen). UID 4 may present output to a user, for instance at respective presence-sensitive displays. UID 4 may present the output as respective graphical user interfaces, which may be associated with functionality provided by computing device 2. For example, UID 4 may present various user interfaces related to the functionality of computing platforms, operating systems, applications, and/or services executing at or accessible by computing device 2 (e.g., electronic message applications, Internet browser applications, mobile or desktop operating systems, etc.). A user may interact with a user interface to cause computing device 2 to perform respective operations relating to functions.

Computing device 2 may include a user interface ("UI") module 6, user response module 8, and notification client module 10. Modules 6, 8, and 10 may perform operations described using software, hardware, firmware, or a mixture of hardware, software, and firmware residing in and/or executing at respective computing device 2. Computing device 2 may each execute respective modules 6, 8, and 10 with one or more processors. Computing device 2 may execute respective modules 6, 8, and 10 as one or more virtual machines executing on underlying hardware of computing device 2. Modules 6, 8, and 10 may execute as one or more services or components of operating systems or computing platforms of computing device 2. Modules 6, 8, and 10 may execute as one or more executable programs at application layers of computing platforms of computing device 2. UID 4 and modules 6, 8, and 10 may be otherwise arranged remotely to and remotely accessible to computing device 2, for instance, as one or more network services operating in a network cloud, and computing device 2 may access the one or more network services using network 18.

Rather than outputting information associated with a notification without determining a user response to the information, techniques of this disclosure may enable computing device 2 to automatically determine a user's reaction to the information and control at least one notification configuration setting related to outputting information associated with other similar notifications. In some examples, computing device 2 may output information associated with a notification, may determine that the user has perceived the information, and may receive an indication of at least one physiological parameter of the user, where the at least one physiological parameter indicates the user's reaction to the information. Computing device 2 may control at least one notification configuration setting related to outputting information associated with other similar notifications, e.g., notifications originating from the same application, the same application type, or the same sender.

Notification client module 22 may perform functions associated with receiving, managing, outputting, and otherwise handling at least a portion of the notifications generated and/or received by processes, platforms, applications, and services executing at computing device 2. Notification client module 22 may receive notifications from notification host module 16 of information server system 14 and output the information associate with the notifications to a recipient process, platform, application, and/or service executing at computing device 2. Notification client module 22 may receive notifications generated by a process, platform, application, and/or service executing at computing device 2, and output the received notifications to information server system 14 over links 20. Notification client module 22 also may cause UI module 6 to output information associated with notifications to indicate the receipt of notifications by computing device 2.

In general, a notification, as used in this disclosure, may relate to any event, including any incoming communication, such as an email, text message, phone call, etc.; an upcoming calendar appointment; a system alert; a reminder; a departure time; upcoming travel information; traffic information; concert information; movie information; or any other activity. The information associated with the notification may include content of the related to the event and included in the notification, including a sender, recipient, subject, text, images, video, audio, and other information of an incoming communication, travel time information, flight information, ticketing information, location information, etc. In some instances the notification is determined (e.g., by a predictive knowledge service) based on one or more prior messages received by or sent by a user associated with computing device 2 (e.g., based on a flight confirmation email, a dinner invitation text message, an electronic receipt, a voicemail message, etc.).

Computing device 2 may receive the notification from notification host module 16 executed by information server system 14 or the notification may be generated by an application, operating system, or other element of computing device 2 and an element, such as notification client module 10, may receive the indication of the event from the other element of computing device 2. When describing computing device 2 or another computing device as receiving a notification, both examples are contemplated.

The notification may be associated with one or more notification attributes. The one or more notification attributes may include information related to the notification, including the origin of the notification. For example, notification attributes may include an application with which the notification is associated (e.g., from which the notification originated), an application type (e.g., communication application, game application, calendar application, media application, etc.) associated with the application with which the notification is associated (e.g., from which the notification originated), a sender (e.g., user) from which the information associated with the notification originated, etc. A single notification may be associated with one or more notification attributes; for example, a notification may be associated with an application, an application type, and a sender.

Responsive to receiving a notification, notification client module 10 may cause UI module 6 to output information associated with the notification. For example, notification client module 10 may cause UI module 6 to output a visual representation of the information for display at a display device. As another example, notification client module 10 may cause UI module 6 to output an audio signal including the information.

User response module 8 may determine whether or not the user has perceived the information. For example, user response module 8 may determine whether the user is interacting with computing device 2 and/or whether computing device 2 is within the field of view of the user. In some examples, user response module 8 may receive information from one or more input devices (e.g., a camera, a microphone, a presence-sensitive input device, etc.), from sensors 12 (e.g., an accelerometer, a gyroscope, a compass, etc.), from an operating system executing at computing device 2, or from other software and/or hardware modules of computing device 2. Using the received information, user response module 8 may determine whether a user is interacting with computing device 2 and/or whether computing device 2 is within the field of view of the user.

User response module 8 may use the determination of whether the user is interacting with computing device 2 and/or whether computing device 2 is within the field of view of the user as a proxy for determining whether the user perceived the information associated with the notification. For example, if the user is interacting with computing device 2, is viewing UID 4, and/or UID 4 is within the field of view of the user when the visual representation of the information is displayed at UID 4, the user is likely to have perceived the information associated with the notification. As another example, if the user is interacting with computing device 2, is viewing UID 4, and/or UID 4 is within the field of view of the user when the audio representation is output by UID 4, the user is likely to have perceived the information associated with the notification.

Computing device 2 also may receive an indication of at least one physiological parameter from one or more sensors 12. In some examples, one or more sensors 12 may be part of computing device 2, as illustrated in FIG. 1. In other examples, one or more sensors 12 may be part of a separate computing device, such as a separate wearable computing device (e.g., a watch, a wristband, a smart watch, a chest strap, smart eye glasses, or any other such devices).

One or more sensors 12 may include any type of sensor configured to sense a physiological signal or state of the user and generate a signal indicative of the sensed physiological parameter. For example, a GSR sensor may be housed on a skin-facing surface of a housing of computing device 2 (or another computing device) and include two or more electrodes for detecting the resistance between the two electrodes. This resistance may change due to perspiration from the user during stressful or active situations of the user, and the GSR sensor may use this change in resistance to generate a corresponding signal indicative of the physiological state. In other examples, the housing of computing device 2 (or another computing device) may contain a temperature sensor (e.g., thermistor or thermocouple) to sense the user's temperature, a pulse oximeter to sense oxygen saturation and/or pulse rate, one or more pressure sensors, or two or more electrodes for detecting an electrogram of the user. One or more sensors 12 may also include one or more gyroscopes, accelerometers, or proximity sensors. Any of these one or more sensors 12 may be used to generate the at least one physiological parameter computing device 2 analyzes to predict, infer, or otherwise determine the user's response to the information associated with the notification.

The at least one physiological parameter may be indicative of a physiological response of the user to the information associated with the notification. The physiological response may correlate to an emotional response of the user to the information. For example, emotional responses may include annoyance, excitement, stress, nervousness, calmness, etc. Because of this, in some examples, one or more sensors 12 may detect the at least one physiological parameter during or shortly after the time which user response module 8 predicts, infers, or otherwise determines that the user is looking at or otherwise interacting with computing device 2 while computing device 2 is outputting the information associated with the notification. In this way, one or more sensors 12 may detect the at least one physiological parameter at a time at which the at least one physiological parameter is indicative of a physiological response of the user to the information associated with the notification.

User response module 8 or another module of computing device 2 may receive the at least one physiological parameter and predict, infer, or otherwise determine the reaction of the user to the information associated with the notification. For example, user response module 8 may be configured to compare one or more values of the physiological parameters received from one or more sensors 12 to one or more thresholds or rules for the respective parameters. In some examples, the one or more thresholds may be selected such that ranges of a physiological parameter less than a threshold value, between two threshold values, and/or greater than a threshold value correspond to a respective predetermined reaction of the user (e.g., annoyed, excited, stressed, nervous, calm, etc.). In some examples, user response module 8 may utilize rules to predict, infer, or otherwise determine the user's reaction to the information for complex situations that involve one threshold, multiple thresholds, or complex relationships between multiple physiological parameters.

In some examples, user response module 8 may determine whether or not the physiological parameters are received during a physical activity of the user or a non-physical activity of the user. When the user is physically active, one or more of the physiological parameters may indicate a stressful condition when the user is instead active and perspiring or having an elevated heart rate. User response module 8 may be configured to reduce these false positives by incorporating activity information to the received physiological parameters. For example, user response module 8 may detect physical activity by analyzing accelerometer data and annotate physiological parameters with a flag that indicates the user was physically active when the physiological parameter was generated. Therefore, user response module 8 may not determine that the user is stressed or excited in these situations or user response module 8 may present the flag to notification client module 10 along with the physiological parameter for determination.

In situations in which the systems discussed herein, such as notification client module 10 and/or user response module 8, may collect personal information about the user, or may make use of the user's personal information, the user may be provided with an opportunity to control whether, and to what extent, programs or features collect the user's information (e.g., information about the user's social network, social actions or activities, profession, the user's preferences, or the user's current location), or to control whether and/or how to receive content from the content server that may be more relevant to the user. In addition, certain data may be treated in one or more ways before it is stored or used, so that personally identifiable information is removed. For example, the user's identity may be treated so that no personally identifiable information can be determined for the user, or the user's geographic location may be generalized where location information is obtained (such as to a city, ZIP code, or state level), so that a particular location of the user cannot be determined. Thus, the user may have control over how information is collected about the user and used by a content server.

Notification client module 10 may be configured to control at least one notification configuration setting related to outputting information associated with other notifications associated with the notification attribute based at least in part on the at least one physiological parameter (e.g., based at least in part on the user's reaction indicated by the at least one physiological parameter). For example, user response module 8 may predict, infer, or otherwise determine that the at least one physiological parameter indicates that the user reacted negatively (e.g., was annoyed, stressed, made nervous, angered, disappointed, etc.) in response to the information associated with the notification.

Responsive to receiving from user response module 8 an indication of this determination, notification client module 10 may control at least one notification configuration setting to increase the prominence of a notification control panel setting related to notifications sharing the notification attribute. For example, notification client module 10 may be configured to control UI module 6 to output a user interface screen including user interface elements allowing a user to control output on information associated with notifications and/or alerts (e.g., visual alerts, audible alerts, haptic alerts, etc.) of the information associated with notifications. Responsive to receiving the indication that the user at least one physiological parameter indicates that the user reacted negatively in response to the information associated with the notification, notification client module 10 may increase a prominence of the user interface elements associated with notifications associated with the notification attribute. For example, notification client module 10 may be configured to control UI module 6 promote a particular application associated with the notification attribute in a list of notification sources, promote a type of application associated with the notification attribute in a list of notification sources, or promote a user (e.g., sender) associated with the notification attribute in a list of notification sources.

As another example, notification client module 10 may cause UI module 6 to output or modify a user interface element included in or adjacent to a visual representation of the information associated with the notification to allow a user to control output of future notifications associated with the notification attribute. For example, notification client module 10 may control UI module 6 to output a toggle switch, a check box, or another user interface element that allows the user to indicate that notification client module 10 should not output information or alerts associated with notifications associated with the notification attribute. This may facilitate user control of notifications from the application, application type, or sender, such as muting or disabling notification alerts and/or output of information associated with notifications from the application, application type, or sender.

As another example, notification client module 10 may receive the indication that the user at least one physiological parameter indicates that the user reacted negatively in response to the information associated with the notification. Notification client module 10 then control at least one notification configuration setting by automatically (without user intervention) disabling or muting notification alerts and/or output of information associated with notifications sharing the notification attribute with the previously output information associated with a notification.

In some examples, because the information associated with the notification may be associated with two or more notification attributes, notification client module 10 may aggregate user responses to multiple notifications associated with a particular application, a particular application type, and/or a particular user (e.g., sender). Notification client module 10 then may apply one or more rules to determine how to control the at least one notification configuration setting. For example, by aggregating user responses to multiple notifications associated with a particular application type, notification client module 10 may predict, infer or otherwise determine that notifications associated with a particular application (e.g., a particular game) associated with the application type (e.g., game application) cause the user to react negatively, but other applications associated with the application type do not cause the user to react negatively. Notification client module 10 then may control the at least one notification configuration setting in a manner that affects only notifications associated with the particular application rather than notifications associated with all applications of the application type.

In this manner, techniques of this disclosure may enable computing device 2 to facilitate user control of notifications (e.g., notification alerts and/or outputting of information associated with notifications). This may enable the user to better control which notifications computing device 2 outputs, which may reduce unwanted interruption to the user and/or user negative reactions due to unwanted notifications. Further, by predicting, inferring, or otherwise determining the reaction of the user to the information associated with the notification, computing device 2 may increase the prominence of notification settings related to notifications to which the user reacted negatively, which may facilitate user control of notification settings pertaining to those notifications.

Figure 2:
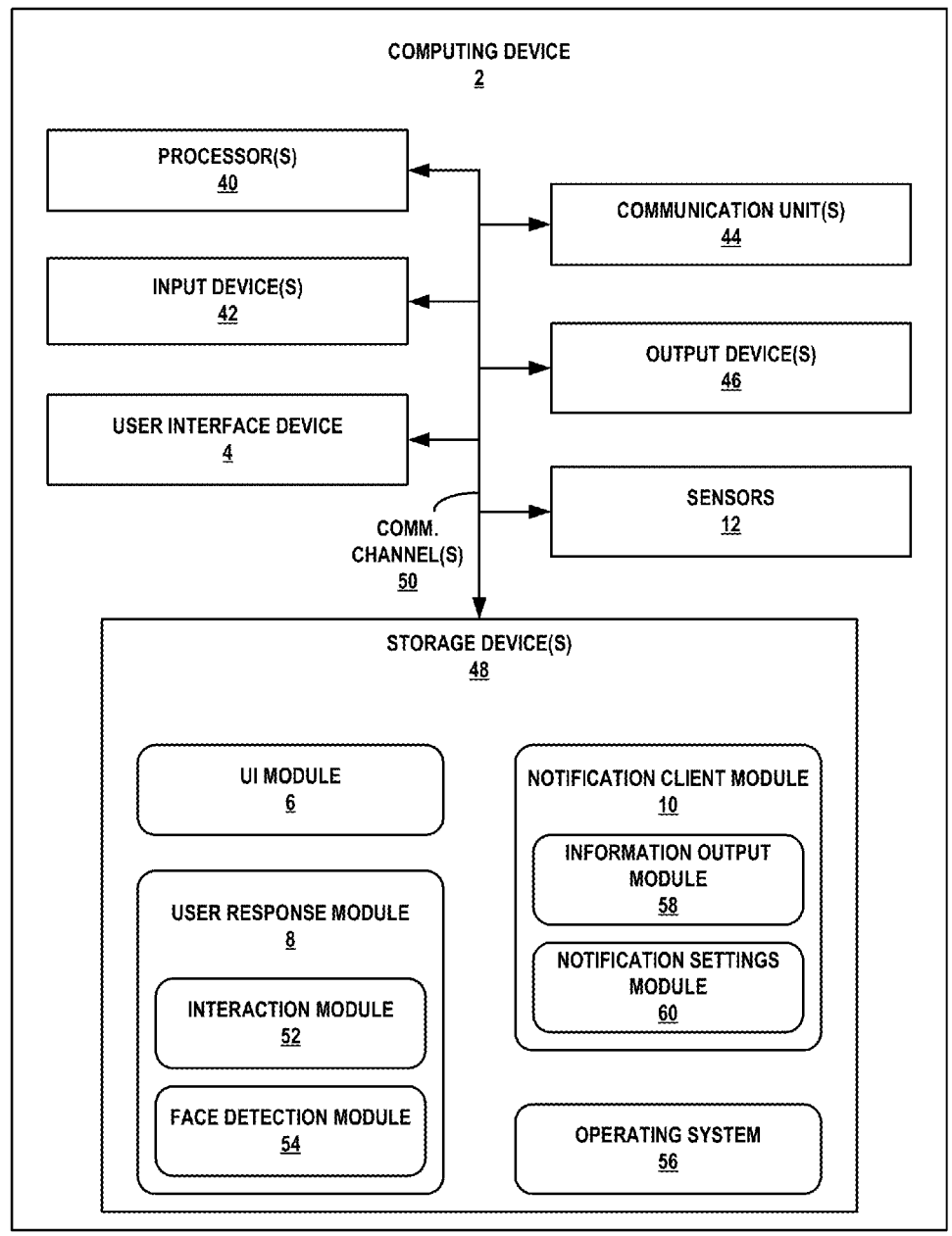
FIG. 2 is a block diagram illustrating an example computing device configured to determine a user reaction to information associated with a notification based on at least one physiological parameter, in accordance with one or more techniques of the present disclosure.

FIG. 2 is a block diagram illustrating an example computing device configured to determine a user reaction to information associated with a notification based on at least one physiological parameter, in accordance with one or more techniques of the present disclosure. Computing device 2 of FIG. 2 is described below within the context of FIG. 1. FIG. 2 illustrates only one particular example of computing device 2, and many other examples of computing device 2 may be used in other instances and may include a subset of the components included in example computing device 2 or may include additional components not shown in FIG. 2.

As shown in the example of FIG. 2, computing device 2 includes one or more processors 40, one or more input devices 42, user interface device 4 ("UID 4"), one or more communication units 44, one or more output devices 46, one or more sensors 12, and one or more storage devices 48. Storage devices 48 of computing device 2 also include UI module 6, user response module 8, notification client module 10, and operating system 56. Computing device 2 may include additional components that, for clarity, are not shown in FIG. 2. For example, computing device 2 may include a battery to provide power to the components of computing device 2. Similarly, the components of computing device 2 shown in FIG. 2 may not be necessary in every example of computing device 2. For example, in some configurations, computing device 2 may not include output devices 46.

Communication channels 50 may interconnect each of the components 4, 12, 40, 42, 44, 46, and 48 for inter-component communications (physically, communicatively, and/or operatively). In some examples, communication channels 50 may include a system bus, a network connection, an inter-process communication data structure, or any other method for communicating data.

One or more processors 40 may implement functionality and/or execute instructions within computing device 2. For example, processors 40 of computing device 2 may receive and execute instructions stored by storage devices 48 that execute the functionality of modules 6, 8, and 10. These instructions executed by processors 40 may cause computing device 2 to read/write/etc. information, such as one or more data files stored within storage devices 48 during program execution. Processors 40 may execute instructions of modules 6, 8, and 10 to cause UID 4 to output one or more graphical indications of incoming communications for display at UID 4 as content of a user interface. That is, modules 6, 8, and 10 may be operable by processors 40 to perform various actions or functions of computing device 2, for instance, causing UID 4 to a present a graphical user interface at UID 4.

One or more communication units 44 of computing device 2 may communicate with external devices via one or more wired and/or wireless networks by transmitting and/or receiving network signals on the one or more networks (e.g., network 18 illustrated in FIG. 1). Examples of communication unit 44 include a network interface card (e.g. such as an Ethernet card), an optical transceiver, a radio frequency transceiver, a GPS receiver, or any other type of device that can send and/or receive information. Other examples of communication units 44 may include short wave radios, cellular data radios, wireless network radios, as well as universal serial bus (USB) controllers.

One or more output devices 46 of computing device 2 may generate output. Examples of output include tactile, audio, and video output. Output devices 46 of computing device 2, in one example, includes a presence-sensitive display, sound card, video graphics adapter card, speaker, cathode ray tube (CRT) monitor, liquid crystal display (LCD), or any other type of device for generating output to a human or machine.

One or more input devices 42 of computing device 2 receive input. Examples of input are tactile, audio, and video input. Input devices 42, in some examples, include a presence-sensitive display, touch-sensitive screen, mouse, keyboard, voice responsive system, video camera, microphone, or any other type of device for detecting input from a human or machine.

In some examples, UID 4 of computing device 2 may include functionality of input devices 42 and/or output devices 46. In the example of FIG. 2, UID 4 may be or may include a presence-sensitive input device. In some examples, a presence sensitive input device may detect an object at and/or near a screen. As one example range, a presence-sensitive input device may detect an object, such as a finger or stylus that is within 2 inches or less of the screen. The presence-sensitive input device may determine a location (e.g., an (x,y) coordinate) of a screen at which the object was detected. In another example range, a presence-sensitive input device may detect an object six inches or less from the screen and other ranges are also possible. The presence-sensitive input device may determine the location of the screen selected by a user's finger using capacitive, inductive, and/or optical recognition techniques. In some examples, presence sensitive input device also provides output to a user using tactile, audio, or video stimuli as described with respect to output device 46, e.g., at a display. In the example of FIG. 2, UID 4 presents a graphical user interface, such as graphical user interfaces 14 of FIG. 1.

While illustrated as an internal component of computing device 2, UID 4 also represents an external component that shares a data path with computing device 2 for transmitting and/or receiving input and output. For instance, in one example, UID 4 represents a built-in component of computing device 2 located within and physically connected to the external packaging of computing device 2 (e.g., a screen on a mobile phone). In another example, UID 4 represents an external component of computing device 2 located outside and physically separated from the packaging of computing device 2 (e.g., a monitor, a projector, etc. that shares a wired and/or wireless data path with a tablet computer).

In some examples, one or more sensors 12 may be configured to measure the movement of computing device 2 and may collect other information associated with computing device 2. For instance, sensors 12 may be configured to measure the position, rotation, velocity, and/or acceleration of computing device 2. Examples of sensors 12 that detect and/or measure movement of computing device 2 may include, but are not limited to, accelerometers and gyroscopes.

In some examples, one or more sensors 12 may also include a clasp sensor (e.g., in examples where computing device 2 is a wearable computing device having a clasp). In some examples, one or more sensors 12 may additionally or alternatively include any other type of sensor capable of collecting information related to computing device 2.

In some examples, one or more sensors 12 may include at least one physiological parameter sensor. For example, one or more sensors 12 may include a galvanic skin response sensor, a pulse sensor, a heart rate sensor, one or more electrode, or any other type of sensor capable of collecting information related to a physiological parameter.

Although one or more sensors 12 are depicted as being part of computing device 2 in the example illustrated in FIGS. 1 and 2, in other examples, at least one of one or more sensors 12 may be a separate device from computing device 2 or may be incorporated in a separate device from computing device 2. For example, computing device 2 may include a mobile phone and at least one of one or more sensors 12 may be included in a wearable computing device, such as a smart watch, a heart rate monitor band, etc. In some examples, some of one or more sensors 12 (e.g., an accelerometer and/or gyroscope) may be included in computing device 2 and some of one or more sensors 12 (e.g., a heart rate monitor and/or a galvanic skin response sensor) may be included in a separate device (e.g., a separate wearable computing device). In other examples, all of one or more sensors 12 may be included in computing device 2.

One or more storage devices 48 within computing device 2 may store information for processing during operation of computing device 2 (e.g., computing device 2 may store data that modules 6, 8, and 10 may access during execution at computing device 2). In some examples, storage device 48 is a temporary memory, meaning that a primary purpose of storage device 48 is not long-term storage. Storage devices 48 on computing device 10 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage devices 48, in some examples, also include one or more computer-readable storage media. Storage devices 48 may be configured to store larger amounts of information than volatile memory. Storage devices 48 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 48 may store program instructions and/or information (e.g., data) associated with modules 6, 8, and 10 and operating system 56.

Operating system 56, in some examples, controls the operation of components of computing device 2. For example, operating system 56, in one example, facilitates the communication of UI module 6, user response module 8, and notification client module 10 with processors 40, one or more output devices 46, UID 4, one or more communication units 44, one or more input devices 42, and one or more sensors 12. UI module 6, user response module 8, and notification client module 10 may each include program instructions and/or data that are executable by computing device 2 (e.g., by one or more processors 40). As one example, UI module 6 can include instructions that cause computing device 2 to perform one or more of the operations and actions described in the present disclosure.

UI module 6 may cause UID 4 to output a user interface (e.g., a graphical user interface and/or an audible user interface), as a user of computing device 2 receives output and/or provides input at UID 4. UI module 6 and UID 4 may receive one or more indications of input from a user as the user interacts with the user interface, at different times and when the user and computing device 2 are at different locations. UI module 6 and UID 4 may interpret inputs detected at UID 4 (e.g., as a user provides one or more gestures at one or more locations of UID 4 at which the graphical user interface is displayed) and may relay information about the inputs detected at UID 4 to one or more associated processes, platforms, operating systems, applications, and/or services executing at computing device 2, to cause computing device 2 to perform functions.

UI module 6 may receive information and instructions from one or more associated processes, platforms, operating systems, applications, and/or services executing at computing device 2 (e.g., user response module 8, notification client module 10, etc.) for generating a user interface (e.g., a graphical and/or audible user interface). In addition, UI module 6 may act as an intermediary between the one or more associated processes, platforms, operating systems, applications, and/or services executing at computing device 2 and various output devices of computing device 2 (e.g., speakers, LED indicators, audio or electrostatic haptic output device, etc.) to produce output (e.g., a graphic, a flash of light, a sound, a haptic response, etc.) with computing device 2.

In accordance with some examples of the disclosure, computing device 2 may be configured to output information associated with a notification, receive an indication of at least one physiological parameter indicative of the response of a user to the information, and control at least one notification configuration setting based on the at least one physiological parameter. For example, notification client module 10 may receive a notification from a remote device (e.g., information server system 14 of FIG. 1 via network 18) or a component of computing device 2 (e.g., an application executed by one or more processors 40). The notification may include information associated with the notification and at least one notification attribute associated with the notification.

The at least one notification attribute may include information related to the notification, including the origin of the notification. For example, notification attributes may include an application with which the notification is associated (e.g., the application from which the notification originated), an application type (e.g., communication application, game application, calendar application, media application, etc.) associated with the application with which the notification is associated (e.g., from which the notification originated), a sender (e.g., user) from which the information associated with the notification originated, etc. A single notification may be associated with one or more notification attributes; for example, a notification may be associated with an application, an application type, and a sender.

Notification client module 10 may cause UI module 8 to output information associated with the notification. The information may include content of or related to the notification, including a sender, recipient, subject, text, images, video, audio, and other information of an incoming communication, travel time information, flight information, ticketing information, location information, etc.

Information output module 58 of notification client module 10 may cause UI module 6 to output the information associated with the notification as a visual representation of the information (e.g., output at UI device 4) or an audio representation of the information (e.g., output at one or more output devices 46). In some examples, information output module 58 may cause UI module 6 to output the information as both a visual representation and an audio representation. In other examples, information output module 58 may cause UI module 6 to output the information as either a visual representation or an audio representation.

After information output module 58 causes UI module 6 to output the information associated with the notification, user response module 8 may predict, infer or otherwise determine if the user has perceived the information. User response module 8 may include an interaction module 52 and a face detection module 54. One or both of interaction module 52 and face detection module 54 may analyze one or more signals to predict, infer or otherwise determine if the user has perceived the information. As described above, in some examples, user response module 8 may predict, infer or otherwise determine whether a user of computing device 2 is interacting with computing device 2 and/or whether computing device 2 is within the field of view of the user while computing device 2 is outputting the information (e.g., visually or audibly) and use this determination as a proxy for whether the user perceived the information associated with the notification.

Interaction module 52 may determine whether the user is interacting with computing device 2. For example, in order to determine if a user is interacting with computing device 2, interaction module 52 may analyze information received from sensors 12, input devices 42, and/or UID 4. As one example, UID 4 and/or input devices 42 may detect user input. The user input may include a gesture unlocking computing device 2, scrolling within a user interface screen displayed at UID 4, or otherwise manipulating a user interface displayed at UID 4. Responsive to detecting the user input, UID 4 and/or input devices 42 may provide an indication of the user input to interaction module 52. Interaction module 52 may determine, based on the indication of the user input, that the user is actively interacting with computing device 2.

In some examples, computing device 2 may be a wearable computing device, such as a computerized watch. In these examples, the user associated with computing device 2 may attempt to view computing device 2. In some examples, the user may attempt to view computing device 2 by moving the arm on which wearable computing device 2 is being worn. For instance, the user may engage in a motion similar to the motion a person performs to look at a watch. The motion may include an internal rotation of the user's wrist and a flexion of the user's shoulder and elbow. One or more sensors 12 of wearable computing device 2 may detect the user's movements and may provide motion data corresponding to the detected movement to interaction module 52.

Interaction module 52 may receive the motion data and may determine, based on the motion data, that the display of computing device 2 is within the field of view of the user (e.g., UID 4, one of output devices 46, etc.). For instance, interaction module 52 may analyze the motion data and determine that the user internally rotated his/her wrist (e.g., the motion data indicates that computing device 2 has rotated). Additionally, interaction module 52 may analyze the motion data and determine that the user has flexed his/her shoulder and/or his/her elbow (e.g., the motion data indicates that computing device 2 has moved vertically and/or laterally). As illustrated in FIG. 1, the user has internally rotated his/her wrist and flexed his/her elbow.

In some instances, interaction module 52 may determine an amount of time that has elapsed between when UID 4 outputs, for display, the information associated with the notification and when sensors 12 detect the motion. In these instances, if the amount of time that has elapsed is less than a threshold amount of time, interaction module 52 may determine that the display of computing device 2 is within the field of view of the user, and infer that the user is viewing the information associated with the notification. If sensors 12 do not detection additional motion data that indicates the computing device 2 is no longer within the field of view of the user (e.g., indicative of the user putting his/her arm down by his/her side), interaction module 52 may determine that the user is continuing to give his/her attention to computing device 2. If sensors 12 provide motion data to interaction module 52 indicative of the user putting his/her arm down by his/her side or otherwise indicative that the display of computing device 2 is no longer within the field of view of the user, interaction module 52 may determine that the display of computing device 2 is no longer within the field of view of the user.

In some examples, interaction module 52 may determine that the user is paying attention to computing device 2 using a combination of detected user input and motion data. For example, if the user is providing input to flip between "cards" of a graphical user interface and then pauses (e.g., computing device 2 does not detect user input for a period of time), interaction module 52 may determine whether the user is still viewing a display of computing device 2 based on motion data from sensors 12. For example, if computing device 2 ceases detecting user input, interaction module 52 may analyze motion data received from sensors 12 after the last detected user input. If the motion data corresponds to a movement of the user's arm down and away, interaction module 52 may determine that the user is no longer paying attention to computing device 2 (e.g., viewing content output at the display). If the motion data indicates that the user is generally holding computing device 2 in the same position as computing device 2 was when the last user input was detected, interaction module 52 may determine that the user is continuing to pay attention to computing device 2 (e.g., viewing content output at the display).

In another example, face detection module 54 may receive image data captured by one of input devices 42 (e.g., video data, still image data, etc. captured by a camera) and determine if the image data includes one or more users. In some examples, face detection module 54 may determine if the image data includes a face of the user associated with computing device 2. In some example, face detection module 54 may compare a face detected in the image data to one or more template images that include a face of the user associated with computing device 2. If the face detected in the image data matches one of the faces in the template images, face detection module 54 may determine that the user associated with computing device 2 is viewing a display of computing device 2.

In various examples, face detection module 54 may also include eye-tracking functionality. In these examples, face detection module 54 may analyze data for a series of images and/or video data and determine, based on the image and/or video data, that a user of computing device 2 is currently looking at a display of computing device 2. In some instances, face detection module 54 may track the eye movement of the user in the image and/or video data and determine that the user is reading information displayed by computing device 2.

No matter how user response module 8 determines that a user of computing device 2 is paying attention (e.g., is looking at or interacting with computing device 2 and/or whether computing device 2 is within the field of view of the user) to computing device 2, user response module 8 may, in some examples, predict, infer or otherwise determine for how long the user is paying attention to computing device 2. User response module 8 may determine for how long the user is paying attention to computing device 2 using any of the techniques described above for predicting, inferring or otherwise determining that the user is interacting with or paying attention to computing device 2. User response module 8 then may compare the duration for which the user is paying attention to computing device 2 to a threshold duration.

The threshold duration may be selected to be a value that represents an approximate minimum time for which the user may need to view the information associated with the notification to perceive the information. In some examples, the threshold duration may be based at least in part on the information that is output by UI module 6. For example, if the information associated with the notification includes an icon representing a missed phone call, the caller's name, the caller's phone number, the threshold duration may be relatively short, e.g., one second. As another example, if the information associated with the notification include content of a text message, the threshold duration may be relatively longer (e.g., three seconds or five seconds). In this way, by comparing the time for which the user is paying attention to computing device 2 to the threshold duration may increase the likelihood that the user has, in fact, perceived the information associated with the notification.

Responsive to predicting, inferring or otherwise determining that the user has perceived the information associated with the notification, user response module 8 may receive or retrieve an indication of at least one physiological parameter representative of a reaction of the user to the information associated with the notification. In some examples, user response module 8 may be continuously or periodically receiving indications of at least one physiological parameter from one or more sensors 12. Responsive to predicting, inferring or otherwise determining that the user has perceived the information associated with the notification, user response module 8 may select the indications of the at least one physiological parameter corresponding to the time during which the user was perceiving (e.g., viewing, listening, etc.) to the information associated with the notification. The user response module 8 may then analyze these indication of the at least one physiological parameter to predict, infer, or otherwise determine the reaction of the user to the information.

In other examples, responsive to predicting, inferring or otherwise determining that the user has perceived the information associated with the notification, user response module 8 may retrieve indications of the at least one physiological parameter, e.g., from one or more sensors 12 or from storage devices 48 (in examples in which storage devices 48 store indications of physiological parameters received from one or more sensors). For example, user response module 8 may query one or more sensors 12 or storage devices 48 to retrieve indications of at least one physiological parameter corresponding to the time during which the user was perceiving to the information associated with the notification.

As described above, the at least one physiological parameter may include, for example, GSR, heart rate, pulse rate, oxygen saturation, temperature, etc. The at least one physiological parameter may be indicative of a physiological response of the user to the information associated with the notification. The physiological response may correlate to an emotional response of the user to the information. For example, emotional responses may include annoyance, anger, disappointment, excitement, stress, nervousness, calmness, etc.

Upon receiving the indication of at least one physiological parameter, user response module 8 may analyze the at least one physiological parameter to predict, infer, or otherwise determine the response of the user to the information related to the notification. For example, user response module 8 may be configured to compare one or more values of the physiological parameters received from one or more sensors 12 to one or more thresholds or rules for the respective parameters. In some examples, the one or more thresholds may be selected such that ranges of a physiological parameter less than a threshold value, between two threshold values, and/or greater than a threshold value correspond to a respective predetermined reaction of the user (e.g., annoyed, angered, disappointed, excited, stressed, made nervous, calmed, etc.). In some examples, user response module 8 may utilize rules to predict, infer, or otherwise determine the user's reaction to the information for complex situations that involve one threshold, multiple thresholds, or complex relationships between multiple physiological parameters.

In some examples, user response module 8 may determine whether or not the physiological parameters are received during a physical activity of the user or a non-physical activity of the user. When the user is physically active, one or more of the physiological parameters may indicate a stressful condition when the user is instead active and perspiring or having an elevated heart rate. User response module 8 may be configured to reduce these false positives by incorporating activity information to the received physiological parameters. For example, user response module 8 may detect physical activity by analyzing accelerometer data and annotate physiological parameters with a flag that indicates the user was physically active when the physiological parameter was generated. Therefore, user response module 8 may not determine that the user is stressed or excited in these situations or user response module 8 may present the flag to notification client module 10.

Notification settings module 60 of notification client module 10 may be configured to receive the user's reaction determined by user response module 8 and control at least one notification configuration setting related to outputting information associated with other notifications associated with the notification attribute based at least in part on the determined user's reaction. For example, user response module 8 may predict, infer, or otherwise determine that the at least one physiological parameter indicates that the user reacted negatively in response to the information associated with the notification. Responsive to receiving from user response module 8 an indication of this determination, notification settings module 60 may control at least one notification configuration setting to increase the prominence of a notification configuration setting related to notifications sharing the notification attribute.

Figure 3A:
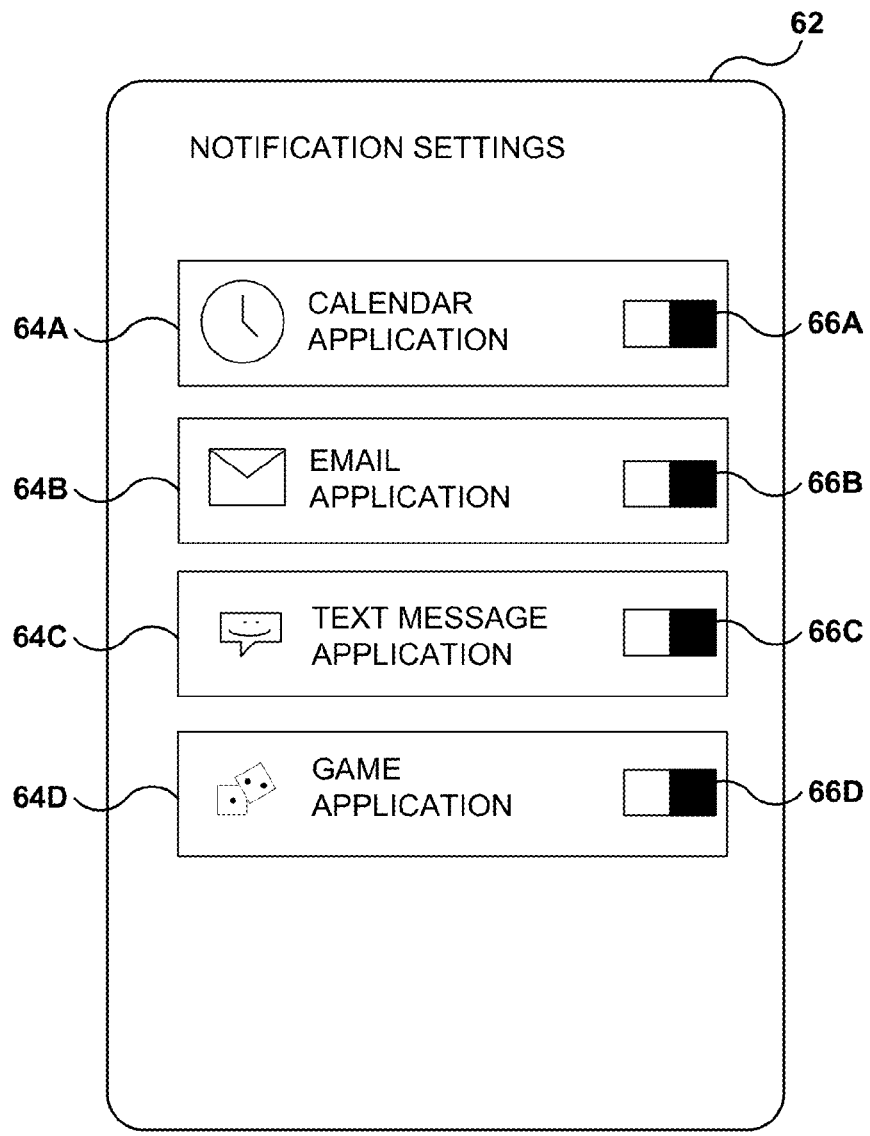
FIGS. 3A and 3B are a conceptual diagrams illustrating example graphical user interfaces that include different orderings of applications within a notification configuration user interface, in accordance with one or more techniques of the present disclosure.
Figure 3B:
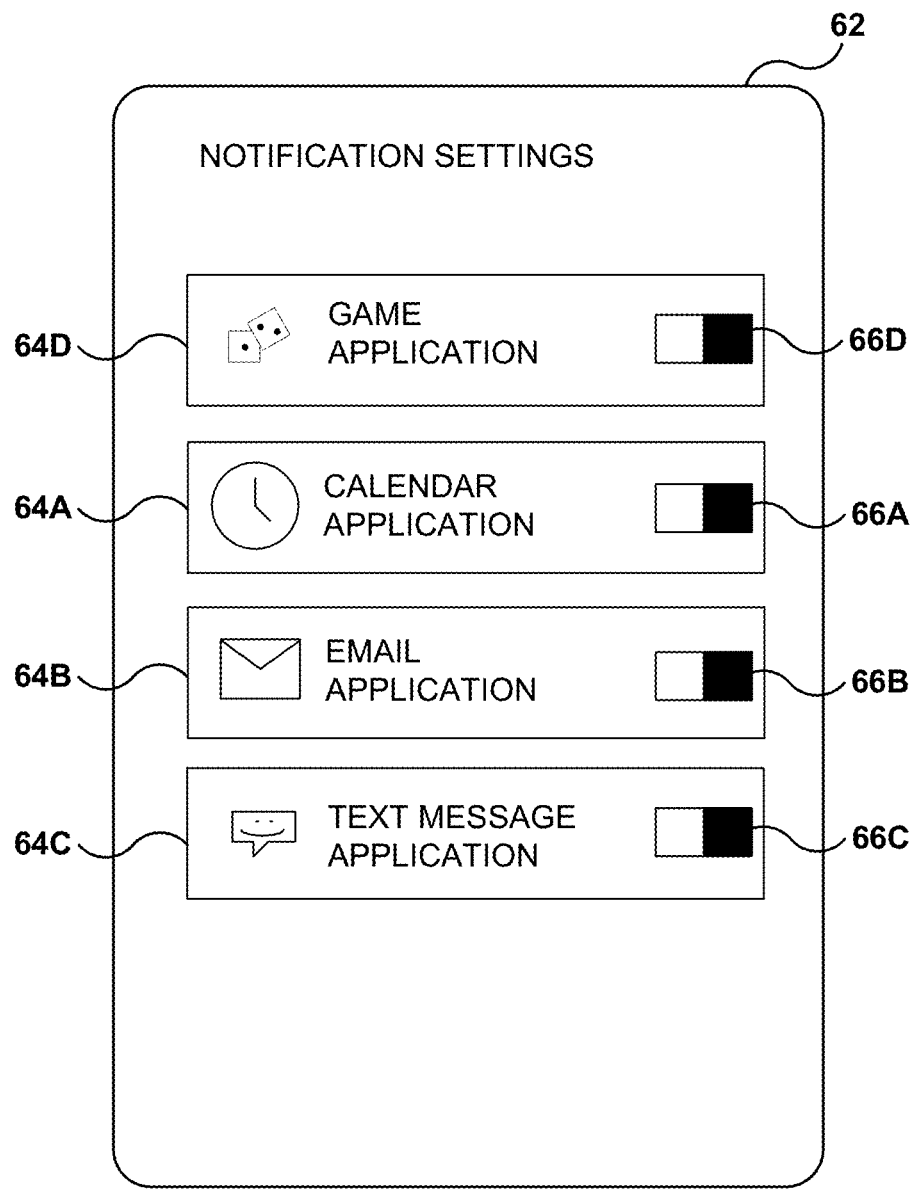

For example, notification settings module 60 may be configured to control UI module 6 to output a user interface screen including user interface elements allowing a user to control output of information associated with notifications and/or alerts (e.g., visual alerts, audible alerts, haptic alerts, etc.) of the information associated with notifications. FIGS. 3A and 3B are conceptual diagrams illustrating example graphical user interfaces that include different orderings of applications within a notification configuration user interface, in accordance with one or more techniques of the present disclosure. Responsive to receiving the indication that the user at least one physiological parameter indicates that the user reacted negatively in response to the information associated with the notification, notification settings module 60 may increase a prominence of the user interface elements in the notification settings UI 62 associated with notifications associated with the notification attribute. For example, as depicted in FIG. 3A, notification settings UI 62 includes UI elements representing four applications: a calendar application 62A, an email application 64B, a text message application 64C, and a game application 64D (collectively, "applications 64"). The UI element for each of applications 64 includes a respective notification output toggle 66A-66D, which allows the user to select whether information output module 58 is to output information associated with a notification upon receipt of the notification. In notification settings UI 62, the UI elements for applications 64 are ordered calendar application 62A, an email application 64B, a text message application 64C, and a game application 64D.

However, if user response module 8 predicts, infers, or otherwise determines that the user reacts in a negative manner to information associated with one or more notifications related to game application 64D, notification settings module 60 may alter the order in which applications 64 are presented in notification settings UI 62. For example, notification settings module 60 may be configured to control UI module 6 output game application UI element 64D higher in the list of applications 64, as shown in FIG. 3B. In this way, notification settings module 60 may increase a likelihood that the user may easily modify or control settings related to similar notifications to those that user response module 8 predicts, infers, or otherwise determines that the user responded negatively to. While the example in FIGS. 3A and 3B are illustrated with respect to particular applications, in other examples, a notification settings UI 62 may include UI elements associated with notifications associated with application types or notifications associated with particular senders, for example.

Figure 4A:
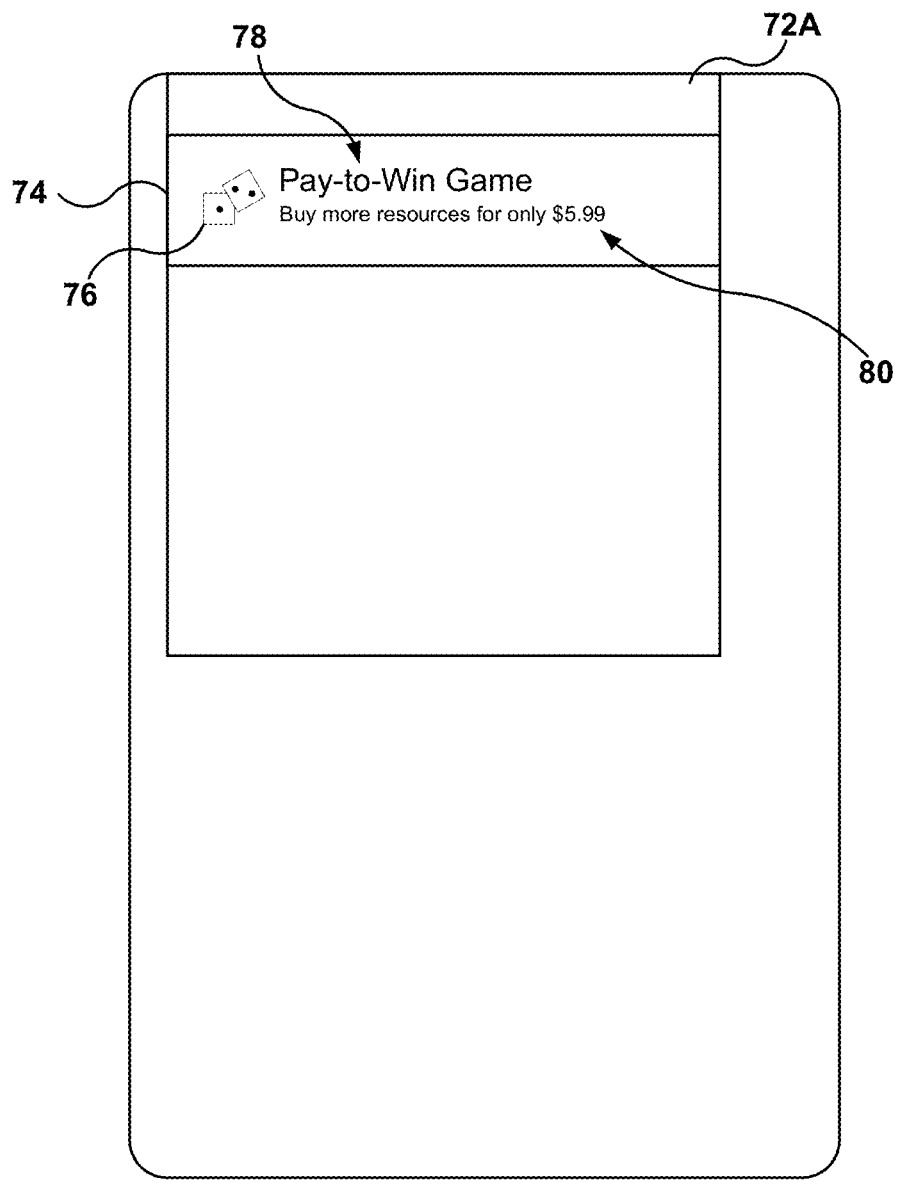
FIGS. 4A and 4B are a conceptual diagrams illustrating example graphical user interfaces that include information associated with a notification, in accordance with one or more techniques of the present disclosure.
Figure 4B:
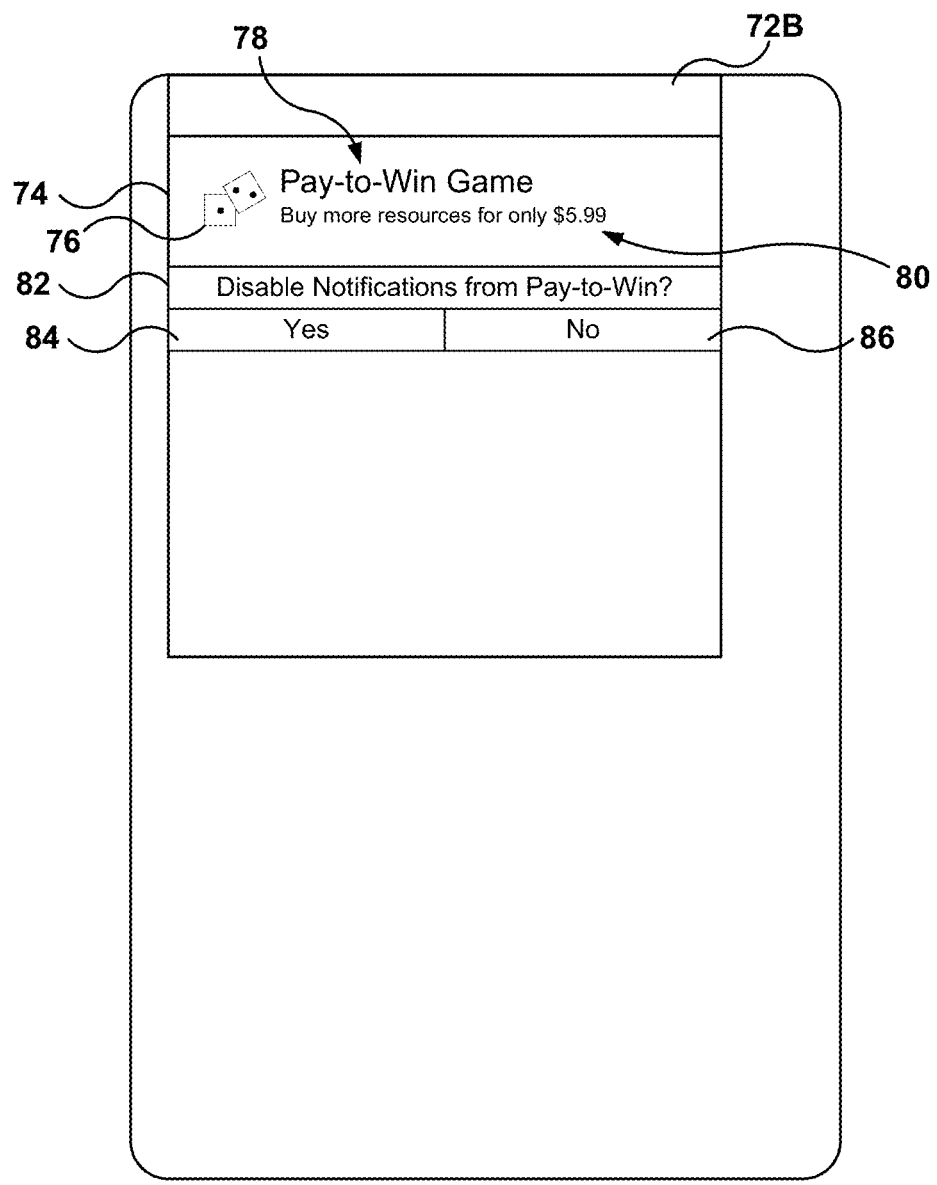

As another example, notification client module 10 may cause UI module 6 to output or modify a user interface element included in or adjacent to a visual representation of the information associated with the notification to allow a user to control output of future notifications associated with the notification attribute. FIGS. 4A and 4B are a conceptual diagrams illustrating example graphical user interfaces that include information associated with a notification, in accordance with one or more techniques of the present disclosure. As shown in FIG. 4A, information output module 58 may control UI module 6 to output information associated with a notification 74 in a notification UI element 72A, such as a notification shade or notification center. In some examples, the notification UI element 72A may include a visual representation of the information associated with the notification 74, such as an icon 76 representing the application with which the notification is associated, a name 78 of the application with which the notification is associated, and content 80 associated with the notification, such as the body of an advertisement. In the example depicted in FIG. 4A, the application is "Pay-to-Win Game" and the content 80 includes an advertisement to "Buy more resources for only $5.99."

As described above, upon output of the information associated with the notification 74, user response module 8 may predict, infer, or otherwise determine that the user has perceived the information associated with the notification 74, and may receive an indication of at least one physiological parameter representative of the reaction of the user to the information associated with the notification 74. In the example depicted in FIGS. 4A and 4B, user response module 8 may predict, infer, or otherwise determine that the user reacts negatively to the information associated with the notification 74 (e.g., based on GSR, and increase in heart rate or pulse rate, etc.). User response module 8 may communicate the user's response to notification settings module 60. Based on the indication of the user's response, notification settings module 60 may cause UI module 6 to output a modified notification UI element 72B, shown in FIG. 4B. In addition to the information depicted in notification UI element 72A (FIG. 4A), notification UI element 72B includes a notification settings UI element 82, which prompts the user to indicate whether to disable notifications from Pay-to-Win. Notification UI element 72B also includes graphical buttons allowing the user to indicate "Yes" 84 or "No" 86. In other examples, rather than graphical buttons, notification UI element 72B may include a toggle switch, a check box, or another user interface element that allows the user to indicate that information output module 58 should not output information or alerts associated with notifications associated with the notification attribute. This may facilitate user control of notifications from the application, application type, or sender, such as muting or disabling notification alerts and/or output of information associated with notifications from the application, application type, or sender.

As another example, notification settings module 60 may receive the indication that the user at least one physiological parameter indicates that the user reacts negatively in response to the information associated with the notification. Notification settings module 60 may then control at least one notification configuration setting by automatically (without user intervention) disabling or muting notification alerts and/or output of information associated with notifications sharing the notification attribute with the previously output information associated with a notification.

In some examples, because the information associated with the notification may be associated with two or more notification attributes, notification settings module 60 may aggregate user responses to multiple notifications associated with a particular application, a particular application type, and/or a particular user (e.g., sender). Notification settings module 60 then may apply one or more rules to determine how to control the at least one notification configuration setting. For example, by aggregating user responses to multiple notifications associated with a particular application type, notification settings module 60 may predict, infer or otherwise determine that notifications associated with a particular application (e.g., a particular game) associated with the application type (e.g., game application) cause the user to react negatively, but other applications associated with the application type do not cause the user to react negatively. Notification settings module 60 then may control the at least one notification configuration setting in a manner that affects only notifications associated with the particular application rather than notifications associated with all applications of the application type.

In this manner, techniques of this disclosure may enable computing device 2 to facilitate user control of notifications (e.g., notification alerts and/or outputting of information associated with notifications). This may enable the user to better control which notifications computing device 2 outputs, which may reduce unwanted interruption to the user and/or user negative reactions due to unwanted notifications. Further, by predicting, inferring, or otherwise determining the reaction of the user to the information associated with the notification, computing device 2 may increase the prominence of notification settings related to notifications to which the user reacted negatively, which may facilitate user control of notification settings pertaining to those notifications.

Figure 5:
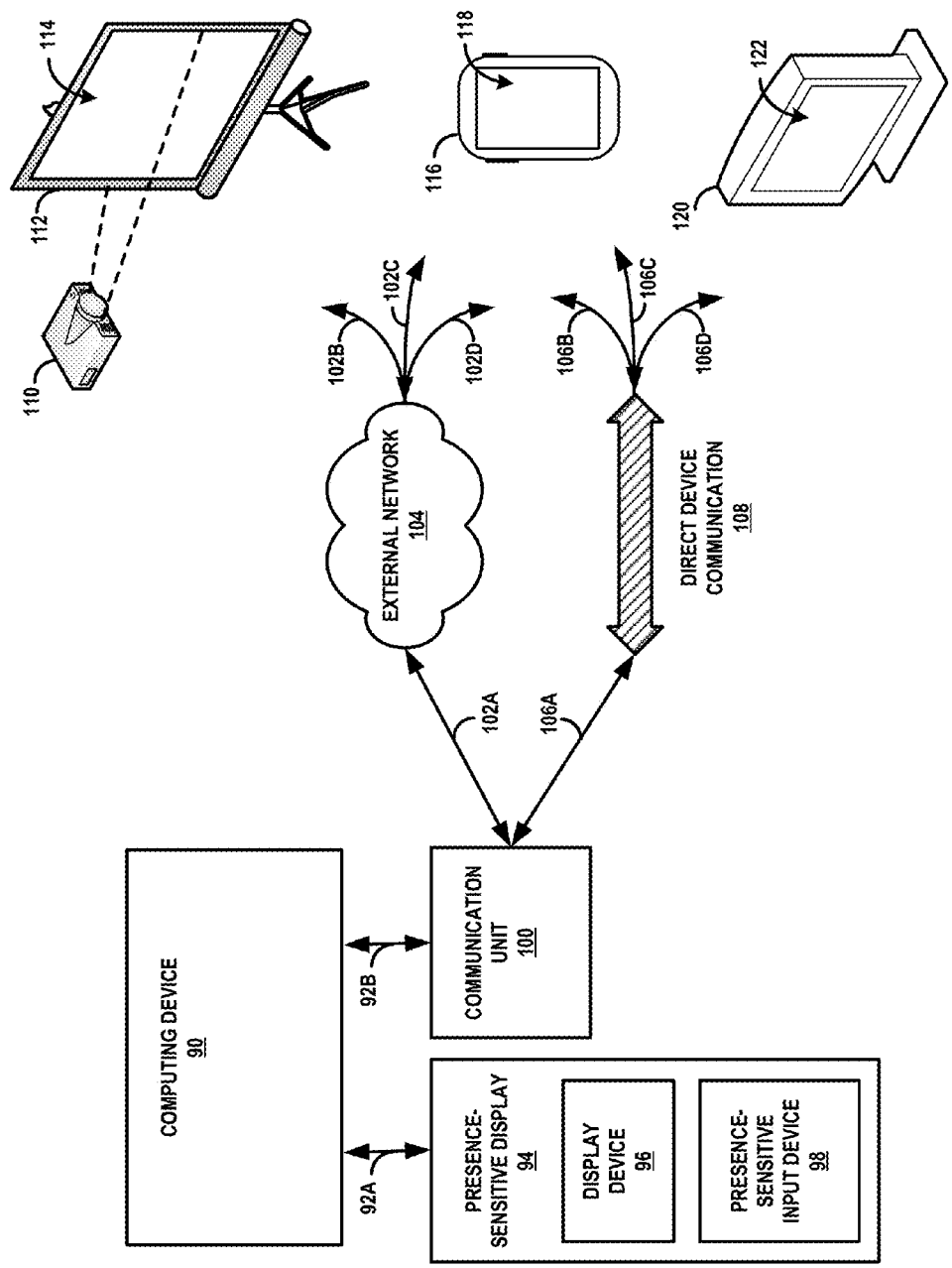
FIG. 5 is a block diagram illustrating an example computing device that outputs information for display at a remote device, in accordance with one or more techniques of the present disclosure.

FIG. 5 is a block diagram illustrating an example computing device that outputs information for display at a remote device, in accordance with one or more techniques of the present disclosure. Graphical content, generally, may include any visual information that may be output for display, such as text, images, a group of moving images, etc. The example shown in FIG. 5 includes a computing device 90, presence-sensitive display 94, communication unit 100, projector 110, projector screen 112, mobile device 116, and visual display device 120. Although shown for purposes of example in FIGS. 1 and 2 as a stand-alone computing device, a computing device, such as computing device 90, may generally be any component or system that includes a processor or other suitable computing environment for executing software instructions and, for example, need not include a presence-sensitive display.

As shown in the example of FIG. 5, computing device 90 may be a processor that includes functionality as described with respect to processor 40 in FIG. 2. In such examples, computing device 90 may be operatively coupled to presence-sensitive display 94 by a communication channel 92A, which may be a system bus or other suitable connection. Computing device 90 may also be operatively coupled to communication unit 100, further described below, by a communication channel 92B, which may also be a system bus or other suitable connection. Although shown separately as an example in FIG. 5, computing device 90 may be operatively coupled to presence-sensitive display 94 and communication unit 100 by any number of one or more communication channels.

In other examples, such as illustrated previously by computing device 2 in FIGS. 1 and 2, a computing device may refer to a portable or mobile device such as mobile phones (including smart phones), wearable devices (including smart watches) laptop computers, etc. In some examples, a computing device may be a desktop computers, tablet computers, smart television platforms, cameras, personal digital assistants (PDAs), servers, mainframes, etc.

Presence-sensitive display 94, like UID 4 as shown in FIG. 1, may include display device 96 and presence-sensitive input device 98. Display device 96 may, for example, receive data from computing device 90 and display the graphical content. In some examples, presence-sensitive input device 98 may determine one or more user inputs (e.g., continuous gestures, multi-touch gestures, single-touch gestures, etc.) at presence-sensitive display 94 using capacitive, inductive, and/or optical recognition techniques and send indications of such user input to computing device 90 using communication channel 92A. In some examples, presence-sensitive input device 98 may be physically positioned on top of display device 96 such that, when a user positions an input unit over a graphical element displayed by display device 96, the location at which presence-sensitive input device 98 corresponds to the location of display device 96 at which the graphical element is displayed. In other examples, presence-sensitive input device 98 may be positioned physically apart from display device 96, and locations of presence-sensitive input device 98 may correspond to locations of display device 96, such that input can be made at presence-sensitive input device 98 for interacting with graphical elements displayed at corresponding locations of display device 96.

As shown in FIG. 5, computing device 90 may also include and/or be operatively coupled with communication unit 100. Communication unit 100 may include functionality of communication unit 44 as described in FIG. 2. Examples of communication unit 100 may include a network interface card, an Ethernet card, an optical transceiver, a radio frequency transceiver, or any other type of device that can send and receive information. Other examples of such communication units may include Bluetooth, 3G, and Wi-Fi radios, Universal Serial Bus (USB) interfaces, etc. Computing device 90 may also include and/or be operatively coupled with one or more other devices, e.g., input devices, output devices, memory, storage devices, etc. that are not shown in FIG. 5 for purposes of brevity and illustration.

FIG. 5 also illustrates a projector 110 and projector screen 112. Other such examples of projection devices may include electronic whiteboards, holographic display devices, and any other suitable devices for displaying graphical content. Projector 110 and projector screen 112 may include one or more communication units that enable the respective devices to communicate with computing device 90. In some examples, the one or more communication units may enable communication between projector 110 and projector screen 112. Projector 110 may receive data from computing device 90 that includes graphical content. Projector 110, in response to receiving the data, may project the graphical content onto projector screen 112. In some examples, projector 110 may determine one or more user inputs (e.g., continuous gestures, multi-touch gestures, single-touch gestures, etc.) at projector screen using optical recognition or other suitable techniques and send indications of such user input using one or more communication units to computing device 90. In such examples, projector screen 112 may be unnecessary, and projector 110 may project graphical content on any suitable medium and detect one or more user inputs using optical recognition or other such suitable techniques.

Projector screen 112, in some examples, may include a presence-sensitive display 114. Presence-sensitive display 114 may include a subset of functionality or all of the functionality of UID 4 as described in this disclosure. In some examples, presence-sensitive display 114 may include additional functionality. Projector screen 112 (e.g., an electronic whiteboard), may receive data from computing device 90 and display the graphical content. In some examples, presence-sensitive display 114 may determine one or more user inputs (e.g., continuous gestures, multi-touch gestures, single-touch gestures, etc.) at projector screen 112 using capacitive, inductive, and/or optical recognition techniques and send indications of such user input using one or more communication units to computing device 90.

FIG. 5 also illustrates mobile device 116 and visual display device 120. Mobile device 116 and visual display device 120 may each include computing and connectivity capabilities. Examples of mobile device 116 may include e-reader devices, convertible notebook devices, hybrid slate devices, wearable devices, etc. Examples of visual display device 120 may include other semi-stationary devices such as televisions, computer monitors, etc. As shown in FIG. 5, mobile device 116 may include a presence-sensitive display 118. Visual display device 120 may include a presence-sensitive display 122. Presence-sensitive displays 118, 122 may include a subset of functionality or all of the functionality of UID 4 as described in this disclosure. In some examples, presence-sensitive displays 118, 122 may include additional functionality. In any case, presence-sensitive display 122, for example, may receive data from computing device 90 and display the graphical content. In some examples, presence-sensitive display 122 may determine one or more user inputs (e.g., continuous gestures, multi-touch gestures, single-touch gestures, etc.) at projector screen using capacitive, inductive, and/or optical recognition techniques and send indications of such user input using one or more communication units to computing device 90.

As described above, in some examples, computing device 90 may output graphical content for display at presence-sensitive display 94 that is coupled to computing device 90 by a system bus or other suitable communication channel. Computing device 80 may also output graphical content for display at one or more remote devices, such as projector 110, projector screen 112, mobile device 116, and visual display device 120. For instance, computing device 90 may execute one or more instructions to generate and/or modify graphical content in accordance with techniques of the present disclosure. Computing device 90 may output the data that includes the graphical content to a communication unit of computing device 90, such as communication unit 1000. Communication unit 100 may send the data to one or more of the remote devices, such as projector 110, projector screen 112, mobile device 116, and/or visual display device 120. In this way, computing device 90 may output the graphical content for display at one or more of the remote devices. In some examples, one or more of the remote devices may output the graphical content at a presence-sensitive display that is included in and/or operatively coupled to the respective remote devices.

In some examples, computing device 90 may not output graphical content at presence-sensitive display 94 that is operatively coupled to computing device 90. In other examples, computing device 90 may output graphical content for display at both a presence-sensitive display 94 that is coupled to computing device 90 by communication channel 92A, and at one or more remote devices. In such examples, the graphical content may be displayed substantially contemporaneously at each respective device. For instance, some delay may be introduced by the communication latency to send the data that includes the graphical content to the remote device. In some examples, graphical content generated by computing device 90 and output for display at presence-sensitive display 94 may be different than graphical content display output for display at one or more remote devices.

Computing device 90 may send and receive data using any suitable communication techniques. For example, computing device 90 may be operatively coupled to external network 104 using network link 102A. Each of the remote devices illustrated in FIG. 5 may be operatively coupled to network external network 104 by one of respective network links 102B, 102C, and 102D. External network 104 may include network hubs, network switches, network routers, etc., that are operatively inter-coupled thereby providing for the exchange of information between computing device 90 and the remote devices illustrated in FIG. 5. In some examples, network links 102A-102D may be Ethernet, ATM or other network connections. Such connections may be wireless and/or wired connections.

In some examples, computing device 90 may be operatively coupled to one or more of the remote devices included in FIG. 5 using direct device communication 108. Direct device communication 108 may include communications through which computing device 90 sends and receives data directly with a remote device, using wired or wireless communication. That is, in some examples of direct device communication 108, data sent by computing device 90 may not be forwarded by one or more additional devices before being received at the remote device, and vice-versa. Examples of direct device communication 108 may include Bluetooth, Near-Field Communication, Universal Serial Bus, Wi-Fi, infrared, etc. One or more of the remote devices illustrated in FIG. 5 may be operatively coupled with computing device 90 by communication links 106A-106D. In some examples, communication links 106A-106D may be connections using Bluetooth, Near-Field Communication, Universal Serial Bus, infrared, etc. Such connections may be wireless and/or wired connections.

In some examples, one or more sensors 12 may be located remote to computing device 90 and may be operatively coupled with computing device 90 by communication links 106A-106D and/or network links 102A-102D. For example, one or more sensors 12 may be included in mobile device 116 or may be separate from any of the devices illustrated in FIG. 5. Examples of one or more sensors 12 may include at least one physiological parameter sensor. For example, one or more sensors 12 may include a galvanic skin response sensor, a pulse sensor, a heart rate sensor, one or more electrode, or any other type of sensor capable of collecting information related to a physiological parameter.

In accordance with techniques of the disclosure, computing device 90 may be operatively coupled to projector 110, mobile device 116, and/or visual display device 120 using external network 104. Computing device 90 may output information associated with a notification at one or more of projector 110, mobile device 116, and/or visual display device 120. While the information associated with the notification is displayed at projector 110, mobile device 116, and/or visual display device 120, computing device 90 may predict, infer, or otherwise determine whether the user has perceived the information, as described above. For example, computing device 90 may predict, determine, or otherwise infer that the user is interacting with, viewing, or otherwise paying attention to projector 110, mobile device 116, and/or visual display device 120, and may use this determination as a proxy for whether the user has perceived the information.

Computing device 90 also may be configured to receive an indication of at least one physiological parameter that is indicative of the response of the user to the information. The at least one physiological parameter may include, for example, a heart rate of the user or a galvanic skin response of the user. The indication of the at least one physiological parameter from at least one physiological parameter sensor, which may be operably coupled to computing device 90 (e.g., via communication links 106A-106D and/or network links 102A-102D).

Computing device 90 may be configured to then control at least one notification configuration setting related to outputting information associated with other notifications associated with the notification attribute, as described above. In this way, by controlling at least one notification configuration setting related to outputting information associated with other notifications associated with the notification attribute, the computing device may facilitate user control of notifications. For example, the techniques of this disclosure may facilitate user control of notifications settings in a way that may make it easier for the user to mute or disable notifications that cause the user to react negatively, are overly interruptive, or otherwise bothersome to the user. This may reduce inconvenience or negative reactions of the user in response to notifications and may facilitate customization of notification settings by the user.

Figure 6:
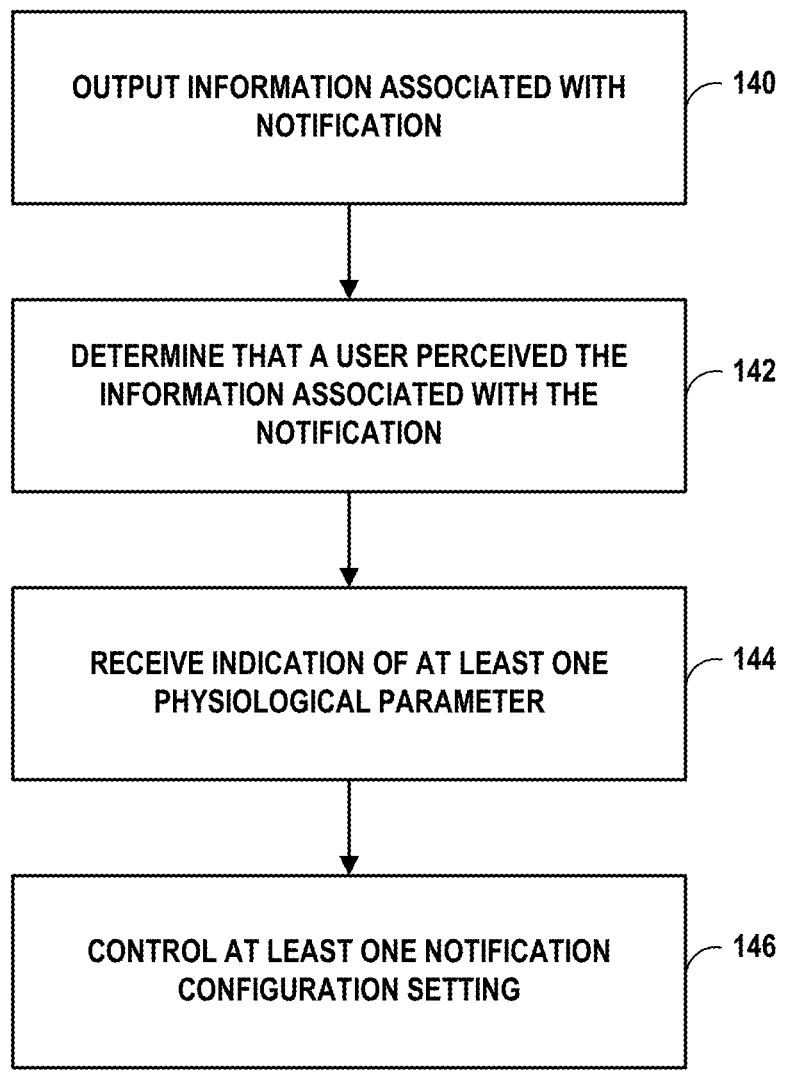
FIG. 6 is a flow diagram illustrating example operations of a computing device configured to determine a user reaction to information associated with a notification based on at least one physiological parameter, in accordance with one or more techniques of the present disclosure.

FIG. 6 is a flow diagram illustrating example operations of a computing device configured to determine a user reaction to information associated with a notification based on at least one physiological parameter, in accordance with one or more techniques of the present disclosure. The techniques of FIG. 6 may be performed by one or more processors of a computing device, such as computing devices 2 and 60 illustrated in FIGS. 1, 2, and 5. For purposes of illustration, the techniques of FIG. 6 are described within the context of computing device 2 of FIGS. 1 and 2, although computing devices having different configurations may perform the techniques of FIG. 6.

In accordance with one or more techniques of the disclosure, computing device 2 may output information associated with a notification (140). For example, information output module 58 may control UI module 6 to output an audible or visual representation of the information using UID 4 and/or one or more output devices 46. The notification may be associated with at least one notification attribute, such as an application, an application type, or a sender of the notification.

User response module 8 may determine whether the user has perceived the information associated with the notification (142). As described above, in some examples, user response module 8 may determine whether the user is interacting with computing device 2, viewing a display of computing device 2 (e.g., UID 4), or otherwise paying attention to computing device 2 for at least a threshold amount of time. The threshold amount of time may be a statically configured amount of time (e.g., 1.5 seconds) or may be dynamically determined based on the information associated with the notification.

After determining that the user has perceived the information associated with the notification, user response module 8 also may receive an indication of at least one physiological parameter representative of a reaction of the user to the information (144). User response module 8 may determine the reaction of the user based at least in part on the at least one physiological parameter. For example, user response module 8 may compare the at least one physiological parameter to at least one physiological parameter threshold value to determine the reaction that the physiological parameter is representative of. In some examples, user response module 8 may apply a set of rules to the at least one physiological parameter (e.g., to at least two physiological parameters) to determine the reaction of the user to the information.

Notification settings module 60 may receive an indication of the user reaction, and may control at least one notification configuration setting based at least in part on the indication of the user reaction (146). For example, responsive to determining that at least one physiological parameter indicated that the user reacted negatively, notification setting module 60 may increase the prominence of a notification control panel setting related to notifications sharing the notification attribute. As another example, notification setting module 60 may output or modify a user interface element included in or adjacent to a visual representation of the information associated with the notification to allow a user to control output of future notifications associated with the notification attribute. As another example, responsive to determining that at least one physiological parameter indicated that the user reacted negatively, notification setting module 60 may be configured to disable future notifications associated with the notification attribute. In this way, by controlling at least one notification configuration setting related to outputting information associated with other notifications associated with the notification attribute, computing device 2 may facilitate user control of notifications. For example, the techniques of this disclosure may facilitate user control of notifications settings in a way that may make it easier for the user to mute or disable notifications that are cause negative reactions, are overly interruptive, or otherwise bothersome to the user. This may reduce inconvenience or negative reactions of the user in response to notifications and may facilitate customization of notification settings by the user.

Example 1

A method comprising: outputting information associated with a notification, wherein the notification is associated with a notification attribute; determining, by a computing device, that a user has perceived the information associated with the notification; receiving, by the computing device, an indication of at least one physiological parameter representative of a reaction of the user to the information associated with the notification; and responsive to receiving the indication of the at least one physiological parameter representative of the reaction of the user to the information associated with the notification, controlling, by the computing device, at least one notification configuration setting related to outputting information associated with other notifications associated with the notification attribute.

Example 2

The method of example 1, wherein outputting information associated with the notification comprises outputting, for display at a display device, a visual representation including the information associated with the notification, and wherein determining that the user has perceived the information associated with the notification comprises determining that the display device is within a field of view of the user.

Example 3

The method of example 2, wherein determining that the display device is within the field of view of the user comprises detecting an orientation of the display device using at least one of a gyroscope or an accelerometer.

Example 4

The method of any of examples 1 to 3, wherein outputting information associated with the notification comprises outputting an audible signal including the information associated with the notification, and wherein determining that the user has perceived the information associated with the notification comprises outputting the audible signal.

Example 5

The method of examples 1 to 4, wherein the at least one physiological parameter comprises at least one of a galvanic skin response of the user or a heart rate of the user.

Example 6

The method of any of examples 1 to 5, wherein the notification attribute comprises at least one of an application associated with the notification, an application type associated with the notification, or a sender associated with the notification, and wherein controlling at least one notification configuration setting related to outputting information associated with other notifications associated with the notification attribute comprises disabling notifications associated with the at least one of the application, the application type, or the sender.

Example 7

The method of any of examples 1 to 5, wherein the notification attribute comprises at least one of an application associated with the notification, an application type associated with the notification, or a sender associated with the notification, and wherein controlling at least one notification configuration setting related to outputting information associated with other notifications associated with the notification attribute comprises modifying an order of presentation of at least one of applications, application types, or senders within a notification settings menu.

Example 8

The method of any of examples 1 to 5, wherein the notification attribute comprises at least one of an application associated with the notification, an application type associated with the notification, or a sender associated with the notification, and wherein controlling at least one notification configuration setting related to outputting information associated with other notifications associated with the notification attribute comprises: outputting a user interface element; and responsive to receiving an indication of a user input selecting the user interface element, disabling, by the computing device, output of information associated with notifications from the at least one of an application associated with the notification, the application type associated with the notification, or the sender associated with the notification.

Example 9

A computing device comprising: one or more processors; and at least one module operable by the one or more processors to: output information associated with a notification, wherein the notification is associated with a notification attribute; determine that a user has perceived the information associated with the notification; receive an indication of at least one physiological parameter representative of a reaction of the user to the information associated with the notification; and responsive to receiving the indication of the at least one physiological parameter representative of the reaction of the user to the information associated with the notification, control at least one notification configuration setting related to outputting information associated with other notifications associated with the notification attribute.

Example 10

The computing device of example 9, wherein the at least one module is operable by the one or more processors to output, for display at a display device, a visual representation including the information associated with the notification, and determine that the user has perceived the information associated with the notification by at least determining that the display device is within a field of view of the user.

Example 11

The computing device of example 10, wherein the at least one module is operable by the one or more processors to determine that the display device is within the field of view of the user by at least detecting an orientation of the display device using at least one of a gyroscope or an accelerometer.

Example 12

The computing device of any of examples 9 to 11, wherein the at least one module is operable by the one or more processors to output information associated with the notification by at least outputting an audible signal including the information associated with the notification, and determine that the user has perceived the information associated with the notification by at least outputting the audible signal.

Example 13

The computing device of any of examples 9 to 12, wherein the at least one physiological parameter comprises at least one of galvanic skin response of the user or heart rate of the user.

Example 14

The computing device of any of examples 9 to 13, wherein the notification attribute comprises at least one of an application associated with the notification, an application type associated with the notification, or a sender associated with the notification, and wherein the at least one module is operable by the one or more processors to control at least one notification configuration setting related to outputting information associated with other notifications associated with the notification attribute by at least disabling notifications associated with the at least one of the application, the application type, or the sender.

Example 15

The computing device of any of examples 9 to 13, wherein the notification attribute comprises at least one of an application associated with the notification, an application type associated with the notification, or a sender associated with the notification, and wherein the at least one module is operable by the one or more processors to control at least one notification configuration setting related to outputting information associated with other notifications associated with the notification attribute by at least modifying an order of presentation of at least one of applications, application types, or senders within a notification settings menu.

Example 16

The computing device of any of examples 9 to 13, wherein the notification attribute comprises at least one of an application associated with the notification, an application type associated with the notification, or a sender associated with the notification, and wherein the at least one module is operable by the one or more processors to control at least one notification configuration setting related to outputting information associated with other notifications associated with the notification attribute by at least: outputting a user interface element; and responsive to receiving an indication of a user input selecting the user interface element, disabling output of information associated with notifications from the at least one of an application associated with the notification, the application type associated with the notification, or the sender associated with the notification.

Example 17

A computer-readable storage medium comprising instructions that, when executed, configure one or more processors of a computing device to: output information associated with a notification, wherein the notification is associated with a notification attribute; determine that a user has perceived the information associated with the notification; receive an indication of at least one physiological parameter representative of a reaction of the user to the information associated with the notification; and responsive to receiving the indication of the at least one physiological parameter representative of the reaction of the user to the information associated with the notification, control at least one notification configuration setting related to outputting information associated with other notifications associated with the notification attribute.

Example 18

The computer-readable storage medium of example 17, wherein the instructions that, when executed, configure one or more processors of the computing device to output information associated with the notification comprise instructions that, when executed, configure one or more processors of the computing device to output, for display at a display device, a visual representation including the information associated with the notification, and wherein the instructions that, when executed, configure one or more processors of the computing device to determine that the user has perceived the information associated with the notification comprise the instructions that, when executed, configure one or more processors of the computing device to determine that the display device is within a field of view of the user.

Example 19

The computer-readable storage medium of example 17 or 18, wherein the at least one physiological parameter comprises at least one of galvanic skin response of the user or heart rate of the user.

Example 20

The computer-readable storage medium of any of examples 17 to 19, wherein the notification attribute comprises at least one of an application associated with the notification, an application type associated with the notification, or a sender associated with the notification, and wherein the instructions that, when executed, configure one or more processors of the computing device to control at least one notification configuration setting related to outputting information associated with other notifications associated with the notification attribute comprise instructions that, when executed, configure one or more processors of the computing device to disable notifications associated with the at least one of the application, the application type, or the sender.

Example 21

The computer-readable storage medium of any of examples 17 to 19, wherein the notification attribute comprises at least one of an application associated with the notification, an application type associated with the notification, or a sender associated with the notification, and wherein the instructions that, when executed, configure one or more processors of the computing device to control at least one notification configuration setting related to outputting information associated with other notifications associated with the notification attribute comprise instructions that, when executed, configure one or more processors of the computing device to modify an order of presentation of at least one of applications, application types, or senders within a notification settings menu.

Example 22

The computer-readable storage medium of any of examples 17 to 19, wherein the notification attribute comprises at least one of an application associated with the notification, an application type associated with the notification, or a sender associated with the notification, and wherein the instructions that, when executed, configure one or more processors of the computing device to control at least one notification configuration setting related to outputting information associated with other notifications associated with the notification attribute comprise instructions that, when executed, configure one or more processors of the computing device to: output a user interface element; and responsive to receiving an indication of a user input selecting the user interface element, disabling output of information associated with notifications from the at least one of an application associated with the notification, the application type associated with the notification, or the sender associated with the notification.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described. These and other examples are within the scope of the following claims.

The invention claimed is:

1. A method comprising:
outputting, by a display device of a wearable computing device, a visual indication of information associated with a notification, wherein the notification is associated with a notification attribute;
while the visual indication is being output:
determining, based at least in part on motion data generated by one or more motion sensors of the wearable computing device, that the display device is within a field of view of the user; and
determining, based at least in part on the motion data, whether the display device remains within the field of view of a user for at least a threshold duration;
determining, by the wearable computing device, that the user has perceived the information associated with the notification based at least in part on determining that the display device remains within the field of view of the user for at least the threshold duration;
responsive to determining that the user has perceived the information associated with the notification, detecting, by the wearable computing device, at least one physiological parameter representative of a reaction of the user to the information associated with the notification; and
controlling, by the wearable computing device and based on the at least one physiological parameter, at least one notification configuration setting related to outputting information associated with other notifications associated with the notification attribute.

2. The method of claim 1, wherein the one or more motion sensors comprises at least one of a gyroscope or an accelerometer, and wherein determining the that the display device is within the field of view of the user comprises detecting, by the wearable computing device, an orientation of the display device using at least one of the gyroscope or the accelerometer.

3. The method of claim 1, wherein the at least one physiological parameter comprises at least one of a galvanic skin response of the user or a heart rate of the user.

4. The method of claim 1,
wherein the notification attribute comprises at least one of an application associated with the notification, an application type associated with the notification, or a sender associated with the notification, and
wherein controlling at least one notification configuration setting related to outputting information associated with other notifications associated with the notification attribute comprises disabling, by the wearable computing device, notifications associated with the at least one of the application, the application type, or the sender.

5. The method of claim 1,
wherein the notification attribute comprises at least one of an application associated with the notification, an application type associated with the notification, or a sender associated with the notification, and
wherein controlling at least one notification configuration setting related to outputting information associated with other notifications associated with the notification attribute comprises modifying, by the wearable computing device, an order of presentation of at least one of applications, application types, or senders within a notification settings menu.

6. The method of claim 1,
wherein the notification attribute comprises at least one of an application associated with the notification, an application type associated with the notification, or a sender associated with the notification, and
wherein controlling at least one notification configuration setting related to outputting information associated with other notifications associated with the notification attribute comprises:
outputting, by the display device, a user interface element; and
responsive to receiving an indication of a user input selecting the user interface element, disabling, by the wearable computing device, output of information associated with notifications from the at least one of an application associated with the notification, the application type associated with the notification, or the sender associated with the notification.

7. The method of claim 1, wherein the motion data is first motion data, the method further comprising:
responsive to determining that the user has perceived the information associated with the notification, determining, by the computing device and based at least in part on second motion data generated by the one or more motion sensors, whether the user was physically active while detecting the at least one physiological parameter
wherein controlling the at least one notification configuration setting is further based on the determination of whether the user was physically active while detecting the at least one physiological parameter.

8. The method of claim 1, wherein the threshold duration is based at least in part on the information associated with the notification.

9. A wearable computing device comprising:
a display device;
one or more motion sensors;
one or more processors; and
at least one module operable by the one or more processors to:
output, for display at the display device, an indication of information associated with a notification, wherein the notification is associated with a notification attribute;
while the display device is outputting the visual indication:
determine, based at least in part on motion data generated by the one or more motion sensors, that the display device is within a field of view of the user; and
determine, based at least in part on the motion data, whether the display device remains within the field of view of a user for at least a threshold duration;
determine that the user has perceived the information associated with the notification based at least in part on determining that the display device remains within the field of view of the user for at least the threshold duration;
responsive to determining that the user has perceived the information associated with the notification, detect at least one physiological parameter representative of a reaction of the user to the information associated with the notification; and
control, based on the at least one physiological parameter, at least one notification configuration setting related to outputting information associated with other notifications associated with the notification attribute.

10. The wearable computing device of claim 9, wherein the one or more motion sensors comprises at least one of a gyroscope or an accelerometer, and wherein the at least one module is operable by the one or more processors to determine the that the display is within the field of view of the user by at least detecting, by at least one of the gyroscope or the accelerometer, an orientation of the display device.

11. The wearable computing device of claim 9, wherein the at least one physiological parameter comprises at least one of a galvanic skin response of the user or a heart rate of the user.

12. The wearable computing device of claim 9,
wherein the notification attribute comprises at least one of an application associated with the notification, an application type associated with the notification, or a sender associated with the notification, and
wherein the at least one module is operable by the one or more processors to control at least one notification configuration setting related to outputting information associated with other notifications associated with the notification attribute by at least disabling notifications associated with the at least one of the application, the application type, or the sender.

13. The wearable computing device of claim 9,
wherein the notification attribute comprises at least one of an application associated with the notification, an application type associated with the notification, or a sender associated with the notification, and
wherein the at least one module is operable by the one or more processors to control at least one notification configuration setting related to outputting information associated with other notifications associated with the notification attribute by at least modifying an order of presentation of at least one of applications, application types, or senders within a notification settings menu.

14. The wearable computing device of claim 9,
wherein the notification attribute comprises at least one of an application associated with the notification, an application type associated with the notification, or a sender associated with the notification, and
wherein the at least one module is operable by the one or more processors to control at least one notification configuration setting related to outputting information associated with other notifications associated with the notification attribute by at least:
outputting, for display at the display device, an indication of a user interface element; and
responsive to receiving an indication of a user input selecting the user interface element, disabling output of information associated with notifications from the at least one of an application associated with the notification, the application type associated with the notification, or the sender associated with the notification.

15. The computing device of claim 9, wherein the motion data is first motion data, and wherein the at least one module is operable by the one or more processors to:
responsive to determining that the user has perceived the information associated with the notification, determine, based at least in part on second motion data generated by the one or more motion sensors, whether the user was physically active while detecting the at least one physiological parameter,
wherein the at least one module is further operable by the one or more processors to control the at least one notification configuration setting based on the determination of whether the user was physically active while detecting the at least one physiological parameter.

16. The computing device of claim 9, wherein the threshold duration is based at least in part on the visual indication of information associated with the notification.

17. A non-transitory computer-readable storage medium comprising instructions that, when executed, configure one or more processors of a wearable computing device to:
output, for display at a display device of the wearable computing, an indication of information associated with a notification, wherein the notification is associated with a notification attribute;
while the display device is outputting the visual indication:
determine, based at least in part on motion data generated by the one or more motion sensors, that the display device is within a field of view of the user; and
determine, based at least in part on the motion data, whether the display device remains within the field of view of a user for at least a threshold duration;
determine that the user has perceived the information associated with the notification based at least in part on determining that the display device remains within the field of view of the user for at least the threshold duration;
responsive to determining that the user has perceived the information associated with the notification, detect at least one physiological parameter representative of a reaction of the user to the information associated with the notification; and
control, based on the at least one physiological parameter, at least one notification configuration setting related to outputting information associated with other notifications associated with the notification attribute.

18. The non-transitory computer-readable storage medium of claim 17, wherein the at least one physiological parameter comprises at least one of a galvanic skin response of the user or a heart rate of the user.

19. The non-transitory computer-readable storage medium of claim 17,
wherein the notification attribute comprises at least one of an application associated with the notification, an application type associated with the notification, or a sender associated with the notification, and
wherein the instructions that configure the one or more processors of the computing device to control at least one notification configuration setting related to outputting information associated with other notifications associated with the notification attribute comprise instructions that, when executed, configure the one or more processors of the computing device to disable notifications associated with the at least one of the application, the application type, or the sender.

20. The non-transitory computer-readable storage medium of claim 17,
wherein the notification attribute comprises at least one of an application associated with the notification, an application type associated with the notification, or a sender associated with the notification, and
wherein the instructions that configure the one or more processors of the computing device to control at least one notification configuration setting related to outputting information associated with other notifications associated with the notification attribute comprise instructions that, when executed, configure the one or more processors of the computing device to modify an order of presentation of at least one of applications, application types, or senders within a notification settings menu.

21. The non-transitory computer-readable storage medium of claim 17,
wherein the notification attribute comprises at least one of an application associated with the notification, an application type associated with the notification, or a sender associated with the notification, and
wherein the instructions that configure the one or more processors of the computing device to control at least one notification configuration setting related to outputting information associated with other notifications associated with the notification attribute comprise instructions that, when executed, configure the one or more processors of the computing device to:
output, for display at the display device, an indication of a user interface element; and
responsive to receiving an indication of a user input selecting the user interface element, disabling output of information associated notifications from the at least one of an application associated with the notification, the application type associated with the notification, or the sender associated with the notification.

22. The non-transitory computer-readable storage medium of claim 17, wherein the motion data is first motion data, and wherein the instructions, when executed, further configure the one or more processors of the computing device to:
responsive to determining that the user has perceived the information associated with the notification, determine, based at least in part on second motion data generated by the one or more motion sensors, whether the user was physically active while detecting the at least one physiological parameter,
wherein the instructions that configure the one or more processors of the computing device to control the at least one notification configuration setting configure the one or more processors to control the at least one notification configuration settings based on the determination of whether the user was physically active while detecting the at least one physiological parameter.

* * * * *

UNITED STATES PATENT AND TRADEMARK OFFICE
CERTIFICATE OF CORRECTION

PATENT NO. : 9,766,959 B2  
APPLICATION NO. : 14/244514  
DATED : September 19, 2017  
INVENTOR(S) : Faaborg et al.

Page 1 of 1

It is certified that error appears in the above-identified patent and that said Letters Patent is hereby corrected as shown below:

Column 33, Line 56 (Claim 15): Replace "The computing device" with --The wearable computing device--

Column 34, Line 3 (Claim 16): Replace "The computing device" with --The wearable computing device--

Column 34, Line 4 (Claim 16): Replace "based at least in part on the visual indication of information associated with the notification." with --based at least in part on information associated with the notification.--

Signed and Sealed this  
Sixth Day of November, 2018

Andrei Iancu  
*Director of the United States Patent and Trademark Office*